(12) United States Patent
Sandman et al.

(10) Patent No.: US 7,141,366 B1
(45) Date of Patent: Nov. 28, 2006

(54) SURFACE DISPLAY OF SELENOCYSTEINE-CONTAINING PEPTIDES

(75) Inventors: Karen E. Sandman, Arlington, MA (US); Christopher J. Noren, Boxford, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 09/937,187

(22) PCT Filed: May 12, 2000

(86) PCT No.: PCT/US00/13292

§ 371 (c)(1),
(2), (4) Date: Sep. 21, 2001

(87) PCT Pub. No.: WO00/70100

PCT Pub. Date: Nov. 23, 2000

Related U.S. Application Data

(60) Provisional application No. 60/134,286, filed on May 14, 1999.

(51) Int. Cl.
*C12Q 1/68* (2006.01)
(52) U.S. Cl. .............................. 435/6; 435/6; 435/7.2
(58) Field of Classification Search .................. 435/5, 435/7.1, 7.4, 69.1, 69.2, 70.1, 963; 530/350
See application file for complete search history.

(56) References Cited

U.S. PATENT DOCUMENTS

| | | |
|---|---|---|
| 5,272,078 A | 12/1993 | Larsen et al. |
| 5,432,018 A | 7/1995 | Dower et al. |
| 5,700,660 A | 12/1997 | Leonard et al. |

FOREIGN PATENT DOCUMENTS

WO   WO 98/39660   9/1998

OTHER PUBLICATIONS

Sandman et al., FASEB Journal, (Apr. 23, 1999) vol. 13, No. 7, pp. A1479.*
Rodi and Malowski, Curr. Opin. Biotechno., 10: 87-93 (1999).
Wilson and Finlay, Canadian Journal of Microbiology, 44: 313-329 (1998).
Geysen, et al., Proc. Natl. Acad. Sci. USA, 81: 3998-4002 (1984).
Houghten, et al., Nature 354: 84-86 (1991).
Lam, et al., Nature, 354: 82-84 (1991).
Figliozzi, et al., Methods Enzymol., 267: 437-447 (1996).
Bunin, et al., Methods Enzymol., 267: 448-465 (1996).
Dente, et al., Journal of Molecular Biology, 269: 694-703 (1997).
Schmitz, et al., J. Mol. Biol., 260: 664-677 (1996).
Stolz, et al., FEBS Lett., 440: 213-217 (1998).
Dwyer, et al., Chem. Biol., 7: 263-274 (2000).
Heider, et al., EMBO J., 11: 3759-3766 (1992).
Klug, et al., Proc. Natl. Acad. Sci. USA 94: 6676-6681 (1997).
Liu, et al., Nucleic Acids Res., 26: 896-902 (1998).
Gorlatov and Stadtman, et al., Proc. Natl. Acad. Sci. USA 95: 8520-8525 (1998).
Pegoraro, et al., J. Mol. Biol. 284: 779-792 (1998).
Bock, et al., Mol. Microbiol., 5: 515-520 (1991).
Zinoni, et al., Proc. Natl. Acad. Sci. USA 84: 3156-3160 (1987).
Stadtman, Ann. Rev. Biochem. 65: 83-100 (1996).
Sandman, et al., J. Am. Chem. Soc., 122: 960-961 (2000).
Sandman and Noren, Nucleic Acids Res. 28: 755-761 (2000).
Maly, et al., Proc. Natl. Acad. Sci. USA, 97: 2419-2424 (2000).
Demartis, et al., J. Mol. Biol., 286: 617-633 (1999).
Pedersen, et al., Proc. Natl. Acad. Sci. USA 95: 10523-10528 (1998).
Arner, et al., J. Mol. Biol. 292: 1003-1016 (1999).
Zwick, et al., Analytical Biochemistry, 264: 87-97 (1998).
Wilson, Biotechniques 15: 414-420 (1993).
Matsudaira, J. Biol. Chem., 262: 10035-10038 (1987).
Looney, et al., Gene 80: 193-208 (1989).
Waite-Rees, et al., J. Bacteriol. 173: 5207-5219 (1991).
Holliger and Riechmann, Structure 5: 265-275 (1997).
Miller and Albertini, J. Mol. Biol. 164: 59-71 (1983).
Chen, et al., J. Biological Chemistry, 268: 23128-23131 (1993).
Ebright, et al., Gene 114: 81-83 (1992).
van Wezenbeek, et al., Gene 11: 129-148 (1980).
Suppmann, et al., EMBO J. 18: 2284-2293 (1999).
Poole, et al., EMBO J. 14: 151-158 (1995).
Giebel, et al., Biochemistry, 34: 15430-15435 (1995).
McLafferty, et al., Gene 128: 29-36 (1993).
O'Neil, et al., Proteins 14: 509-515 (1992).
Luzzago, et al., Gene 128: 51-57 (1993).
McConnel, et al., Gene 151: 115-118 (1994).
Database CAPLUS on STN. Abstract No. 132:147279. Cho et al., "Construction of a hexapeptide library using phage display for bio-panning". J. Microbiol. Jun. 1999, vol. 37(2), pp. 97-101.

* cited by examiner

*Primary Examiner*—Peter Paras, Jr.
*Assistant Examiner*—Jeffrey S Lundgren
(74) *Attorney, Agent, or Firm*—Harriet M. Strimpel

(57) ABSTRACT

The naturally-occurring amino acid selenocysteine (SEC) is incorporated uniquely and specifically in the context of a polypeptide displayed on the surface of an amplifiable genetic particle (phage, cell or spore) in response to incorporation signals engineered in the encoding DNA. In addition to conferring the unique activities of the selenol group to the chemistry of the displayed peptide, Sec also provides a unique handle for specific chemical modification of the display peptide. In addition to increasing the palette of available residues in a random peptide library to 21 possibilities, present invention also provides a means of tethering virtually any desired chemical functionality to the incorporated Sec.

16 Claims, 12 Drawing Sheets

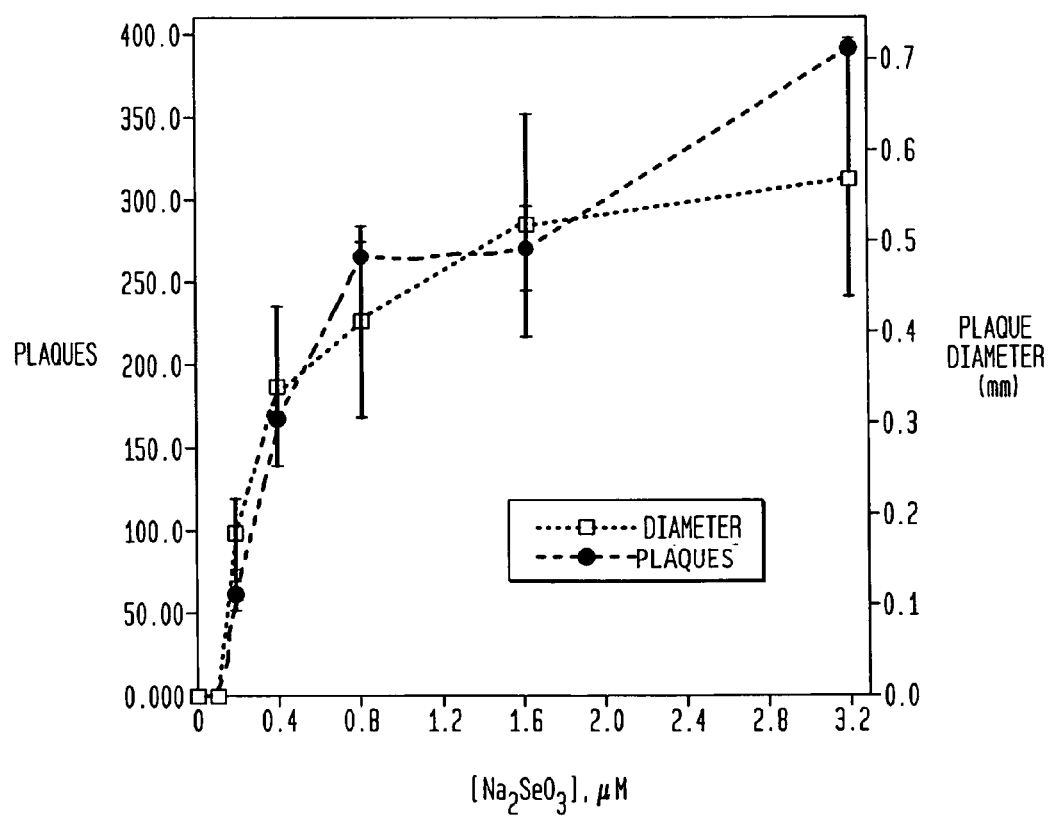

FIG. 9

| CLONE | RANDOM INSERT | | | | | | | Se-DEPENDENT? |
|---|---|---|---|---|---|---|---|---|
| TGAN-1 | TCG<br>S | TCT<br>S | TTT<br>F | CCT<br>P | TGA<br>op[a] | AAG<br>K | TCG<br>S | CCT<br>P | - |
| TGAN-2 | AAG<br>K | TGT<br>C | ACG<br>T | CTT<br>L | TGA<br>Sec | TCT<br>S | ATG<br>M | CTG<br>L | + |
| TGAN-3 | TTG<br>L | CTT<br>L | TTG<br>L | CCT<br>P | TGA<br>op | AAT<br>N | GTT<br>V | CTT<br>L | - |
| TGAN-4 | ATG<br>M | ACT<br>T | ACG<br>T | CAG<br>Q | TGA<br>Sec | CCT<br>S | TCT<br>M | CTG<br>L | + |
| TGAN-5 | CAT<br>H | ATT<br>I | CCG<br>P | CCG<br>P | TGA<br>op | ACG<br>T | AAT<br>N | CCT<br>P | - |
| TGAN-6 | AAG<br>K | GCT<br>A | CTG<br>L | TGT<br>C | TGA<br>Sec | CAG<br>Q | GAT<br>D | TCG<br>S | + |
| TGAN-7 | CTT<br>L | CTT<br>L | CCG<br>P | TGT<br>C | TGA<br>Sec | GCT<br>A | CAG<br>Q | CCG<br>P | +[b] |
| TGAN-8 | CAT<br>H | CAT<br>H | CCG<br>P | ACT<br>T | TGA<br>op | GCT<br>A | AAG<br>K | CAG<br>Q | - |
| TGAN-9 | ATG<br>M | CCT<br>P | CCT<br>P | ACG<br>T | TGA<br>op | ATG<br>M | GCT<br>A | ACG<br>T | - |
| TGAN-10 | AAT<br>N | TGG<br>W | TTT<br>F | TCT<br>S | TGA<br>op | CTG<br>L | ACT<br>T | ACG<br>T | - |
| TGAN-11 | CTG<br>L | CAT<br>H | CCG<br>P | ACG<br>T | TGA<br>op | GCT<br>A | CGG<br>R | CCT<br>P | - |
| TGAN-12 | GAT<br>D | AGG<br>R | GGG<br>G | CCT<br>P | TGA<br>op | GCG<br>A | AAG<br>K | ATT<br>I | - |
| TGAN-13 | GCG<br>A | TCT<br>S | TTG<br>L | CCT<br>P | TGA<br>op | AGG<br>R | ACG<br>T | AGT<br>S | - |

[a] op: opal suppression: Sec or W, depending on Se availability

[b] TGAN-7 production was Se-enhanced;Se supplementation yield larger (3-4x diameter) and more (10x) plaques Selected Library TGAN clones. TGAN-1 was expressed as a pMal-pIII fusion, and tryptophan incorporation was verified by N-terminal sequencing

FIG. 10

| CLONE | RANDOM INSERT | Se-DEPENDENT? |
|---|---|---|
| TGAT-1 | L  P  R  Q  Sec W  S  P<br>TTG CCG CGT CAG TGA TGG TCT CCG | + |
| TGAT-2 | L  T  G  T  Sec C  Q  N<br>TTG ACT GGT ACG TGA TGT CAG AAT | + |
| TGAT-3 | E  A  S  R  Sec C  S  T<br>GAG GCG TCG CGT TGA TGT TCG ACT | + |
| TGAT-4 | K  L  A  R  Sec S  A  S<br>AAG TTG GCT CGT TGA TCG GCG TCG | + |
| TGAT-5 | N  G  A  Q  Sec S  R  H<br>AAT GGG GCG CAG TGA TCG AGG CAT | + |
| TGAT-6 | A  S  P  T  Sec F  K  P<br>GCG AGT CCT ACT TGA TTT AAG CCG | + |
| TGAT-7 | C  A  H  P  Sec S  T  R<br>TGT GCT CAT CCG TGA TCT ACT CGT | + |
| TGAT-8 | Q  S  T  R  Sec W  N  D<br>CAG TCG ACG CGG TGA TGG AAT GAT | + |
| TGAT-9 | I  V  E  S  Sec L  N  P<br>ATT GTG GAG TCG TGA TTG AAT CCG | + |
| TGAT-10 | T  Q  R  M  Sec L  P  P<br>ACG CAG CGT ATG TGA TTG CCG CCC | + |
| TGAT-11 | V  Q  Y  T  Sec L  P  K<br>GTG CAG TAT ACG TGA TTG CCG AAG | + |
| TGAT-12 | A  G  Q  S  Sec S  T  D<br>GCT GGG CAG TCG TGA TCG ACT GAT | + |
| TGAT-13 | L  S  A  S  R  S  Q  F<br>CTG TCT GCG AGT CGA TCG CAG TTT | − |

Selected TGAT library clones. TGAT-13 carried a T→C point mutation within the opal codon

US 7,141,366 B1

SURFACE DISPLAY OF SELENOCYSTEINE-CONTAINING PEPTIDES

This application is a §371 application of international application No. PCT/US00/13292 filed on May 12, 2000, which claims priority from Provisional Application No. 60/134,286 filed May 14, 1999 herein incorporated by reference.

BACKGROUND OF THE INVENTION

The fusion of peptides to the coat proteins of amplifiable genetic particles, e.g., phage, is a widely used method for screening combinatorial libraries of peptides (Rodi and Malowski, *Curr. Opin. Biotechno.*, 10:87–93 (1999); Wilson and Finlay, *Canadian Journal of Microbiology*, 44:313–329 (1998)). One common approach is to express random sequences at the N-terminus of the bacteriophage M13 coat protein pIII, resulting in library complexities of up to $10^9$ different clones. Selection is achieved by performing multiple rounds of target binding (panning), elution and amplification. Each round of panning enriches the pool of clones in favor of the tightest-binding ligands. Because each phage particle contains both the displayed peptide and the DNA encoding it, the selected peptides can be readily identified by DNA sequencing. Despite its utility and convenience, in vivo biological expression limits library diversity to combinations of twenty of the naturally occurring amino acids, linked by peptide bonds.

This problem can be partially circumvented by taking advantage of the enormous potential chemical diversity of synthetic combinatorial libraries. A vast body of work has been carried out with libraries consisting of systematic variations of peptides (Geysen, et al., *Proc. Natl. Acad. Sci. USA*, 81:3998–4002 (1984); Houghten, et al., *Nature* 354: 84–86 (1991), Lam, et al., *Nature*, 354: 82–84 (1991)), peptide analogues (Figliozzi, et al., *Methods Enzymol.*, 267:437–447 (1996), and small molecules (Bunin, et al., *Methods Enzymol.*, 267:448–465 (1996), and an entire industry has been built around this type of combinatorial chemistry. While libraries well in excess of $10^{18}$ different molecules (equivalent to 1 µmol of material if one molecule of each variant is present) can be synthesized, the identification of which molecules bind to a given target from such a vast pool is problematic. Libraries are typically synthesized in spatially addressable form, e.g., grids of pins or wells each containing one compound (Geysen, supra), or tethered to macromolecular beads containing a chemical tag which specifically identifies the attached compound (Lam, et al., supra). Ligand identification thus limits the size of chemically synthesized libraries to a practical upper limit of $10^4$–$10^6$ different molecules. Unlike biosynthetic libraries such as phage display peptide libraries, however, chemically synthesized libraries are not limited to a small subset of potential functional diversity.

The functional diversity of phage displayed peptide libraries can be increased by specifically chemically modifying the library prior to each round of panning. Phage libraries with enzymatically phosphorylated tyrosine residues have been constructed to map protein kinase and SH2 domain recognition sequences (Dente, et al., *Journal of Molecular Biology*, 269:694–703 (1997); Schmitz, et al., *J. Mol. Biol.*, 260:664–677 (1996)). Phage libraries have also been biotinylated at specific lysine residues during in vivo phage morphogenesis, but this method requires a specific 66-residue biotinylation motif (Stolz, et al., *FEBS Lett.*, 440: 213–217 (1998)). Both of these methods require defined flanking sequence, and the incorporated modification cannot be altered. Therefore neither are generally applicable to incorporation of any desired chemical functionality in the context of a randomized amino acid sequence. For example, there are no methods for specifically modifying displayed tyrosine with other chemical moieties while protecting endogenous tyrosine residues elsewhere on the phage coat. The side chains of lysine and cysteine are reactive, but small-molecule reagents are likely to target residues within the native coat protein in addition to the displayed peptide. A new type of phage library, with a unique site available for a broad range of chemical modifications, is therefore needed.

To maintain the essential amplification and selection techniques of phage display, the existing bacterial genetic machinery should be employed to incorporate the unique reactive site into the displayed peptide. A method in which a non-native residue is incorporated into a phage-displayed protein by native chemical ligation (Dwyer, et al., *Chem. Biol.*, 7:263–274 (2000)) could in principle be used to incorporate a unique reactive site, but this method requires that the non-native residue be incorporated within a synthetic peptide sequence, which is then chemically ligated onto a phage displayed polypeptide. As a result, the residues flanking the potential modification site are not encoded on the phage genome, severing the link between displayed sequence and DNA sequence.

SUMMARY OF THE INVENTION

In accordance with the present invention, the power of in vivo biomolecular amplification with the unlimited diversity of small molecule chemistry is united in selenopeptide phage display. The naturally-occurring amino acid selenocysteine (Sec) is incorporated uniquely and specifically in the context of a polypeptide displayed on the surface of an amplifiable genetic particle (phage, polysome, cell or spore) in response to incorporation signals engineered in the encoding DNA. In addition to conferring the unique activities of the selenol group to the chemistry of the displayed peptide, Sec also provides a unique handle for specific chemical modification of the displayed peptide. In addition to increasing the palette of available residues in a random peptide library to 21 possibilities, the present invention also provides a means of tethering virtually any desired chemical functionality to the incorporated Sec. Applications include, but are not limited to, pre-modifying a random peptide library with enzyme substrate analogs or inhibitors prior to panning for higher-affinity inhibitors, as well as selection/ evolution of displayed enzyme specificity by catalytic selection using a substrate tethered to the same particle via an incorporated selenocysteine. Additionally, the coupling of Sec incorporation to phage plaque formation provides a rapid nonradioactive assay for DNA sequence requirements for efficient Sec incorporation.

DESCRIPTION OF THE DRAWINGS

FIG. 3—N-terminal protein sequencing of the fusion of the fdh SECIS with the maltose binding protein. HPLC PTH analysis is displayed in subtractive mode. The expected sequence was SARVSecHGPSV.

FIG. 6—Clone TGAT-6 plaque count and size as a function of supplemental sodium selenite concentration in plating medium. Visible plaques were counted without magnification, and plaque diameter was measured under 7-fold magnification. Error bars represent ±1 standard deviation. Averages were based on triplicate platings, with ten plaques measured per plate.

FIG. 7—Immunoblots of biotinylated phage, probed with HRP-conjugated anti-biotin antibody (NEB) and visualized by chemiluminescence. Phage ($10^{11}$ pfu) were diluted in 150 mM NaCl, 50 mM glycine-HCl (pH 2.5). Iodoacetyl-LC-Biotin (I-Bt) in DMF was added at 5% v/v to the indicated final concentration, and the reactions were incubated in the dark at room temperature. MW: biotinylated molecular weight markers.

FIG. 9—Selected library TGAN clones. TGAN-1 was expressed as a pMal-pIII fusion, and tryptophan incorporation was verified by N-terminal sequencing. $^a$op: opal suppression: Sec or W, depending on Se availability. $_b$TGAN-7 production was Se-enhanced; Se supplementation yielded larger (3–4×diameter) and more (10×) plaques. (SEQ ID NO:2 through SEQ ID NO:14).

FIG. 10-S*elected* TGAT library clones. TGAT-13 carried a T→C point mutation within the opal codon. (SEQ ID NO:15 through SEQ ID NO:27).

DETAILED DESCRIPTION OF THE INVENTION

The present invention which describes a method for biosynthetic incorporation of a unique reactive site takes advantage of the naturally occurring amino acid selenocysteine (Sec). The potential modifications of Sec derive from its unique chemical properties. The pKa of Sec is 5.2, compared to 8.1 for Cys, so that at pH 6–7, nucleophilic substitution reactions can specifically alkylate Sec, but not Cys residues (Gorlatov and Stadtman, et al., *Proc. Natl. Acad. Sci. USA* 95:8520–8525 (1998)). The formation of stable sulfide-selenide cross-links (Pegoraro, et al., *J. Mol. Biol.* 284:779–792 (198)) also permits covalent Sec modification by thiol reagents.

Figure 1:
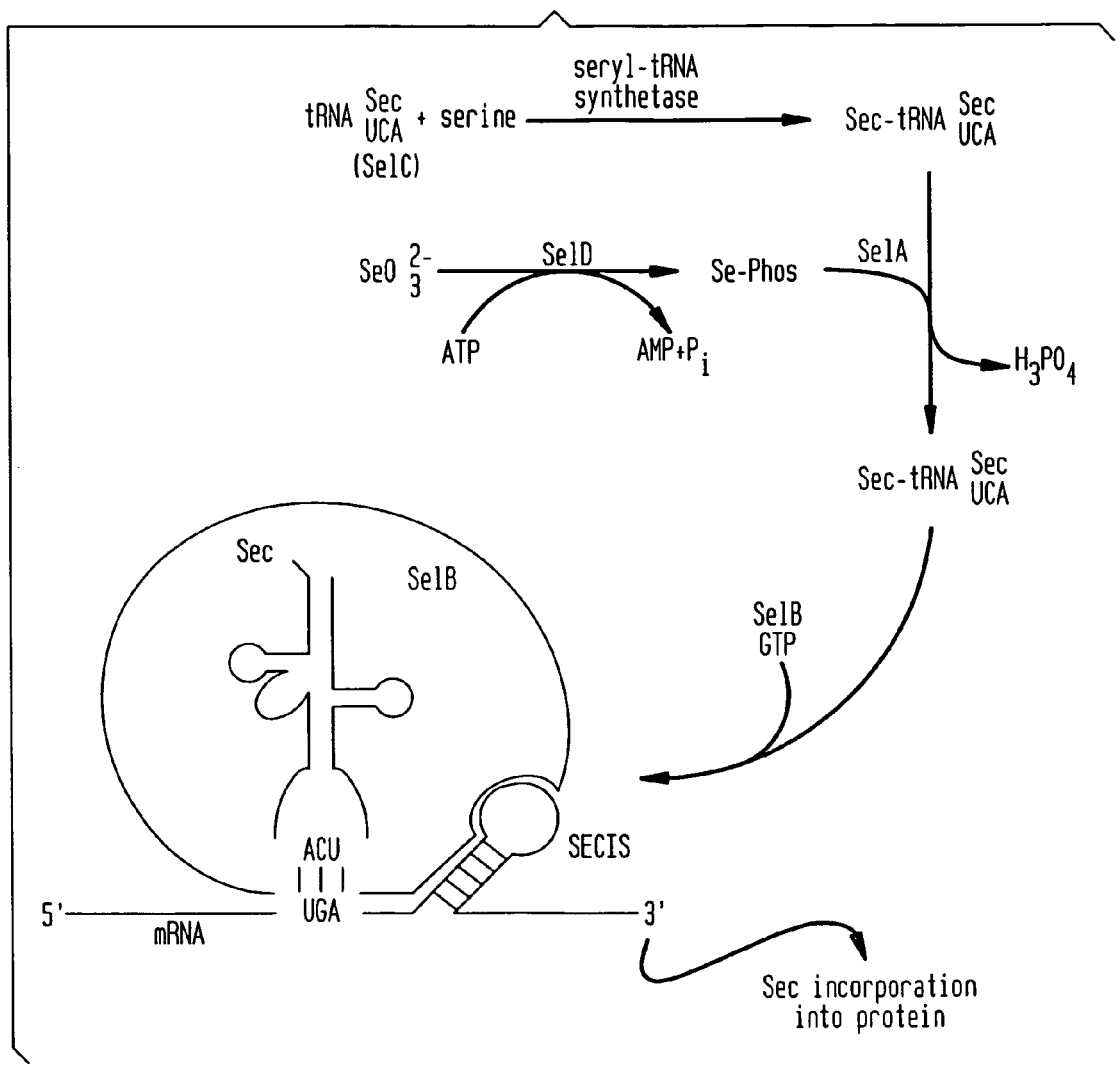
FIG. 1-B*iosynthetic* pathway for cotranslational selenocysteine incorporation. Sel C, the opal codon-specific Sec tRNA, is first charged with serine. ATP-dependent SelD catalysis transforms environmental selenite to an activated Se-phosphate species. This species is utilized by SelA to displace the serine hydroxyl with a selenol moiety, forming a Sec-charged tRNA that recognizes the UGA opal codon. In the presence of GTP, the SelB elongation factor effects Sec translation by binding both the Sec-tRNA and the mRNA SECIS.

Incorporation of selenocysteine involves harnessing the existing biosynthetic mechanism. Eubacterial Selenocysteine (Sec) incorporation, as depicted in FIG. 1, has been well characterized and requires the constitutively expressed selA, selB, se/C and selD gene products (Bock, et al., Mol. Microbiol., 5:515–520 (1991)). Sec is encoded by the TGA opal stop codon (Zinoni, et al., *Proc. Natl. Acad. Sci. USA* 84:3156–3160 (1987)), which is suppressed in the presence of a specific downstream hairpin structure termed the Selenocysteine Insertion Sequence (SECIS). Sec is incorporated via a unique tRNA species, the selC gene product, which is initially aminoacylated with serine by seryl-tRNA synthetase. The loaded serine is converted to selenocysteine by the selA gene product, using a selenium phosphate donor synthesized by the selD gene product. Translation by the resulting Sec-tRNA$^{sec}$ is mediated by the selB product, an analog of (the Elongation Factor EF-Tu which simultaneously recognizes Sec-tRNA$^{Sec}$ and the SECIS. The incorporation mechanism in Eukarya and Archaea is nearly identical (Stadtman, *Ann. Rev. Biochem.* 65:83–100 (1996)).

Figure 2:
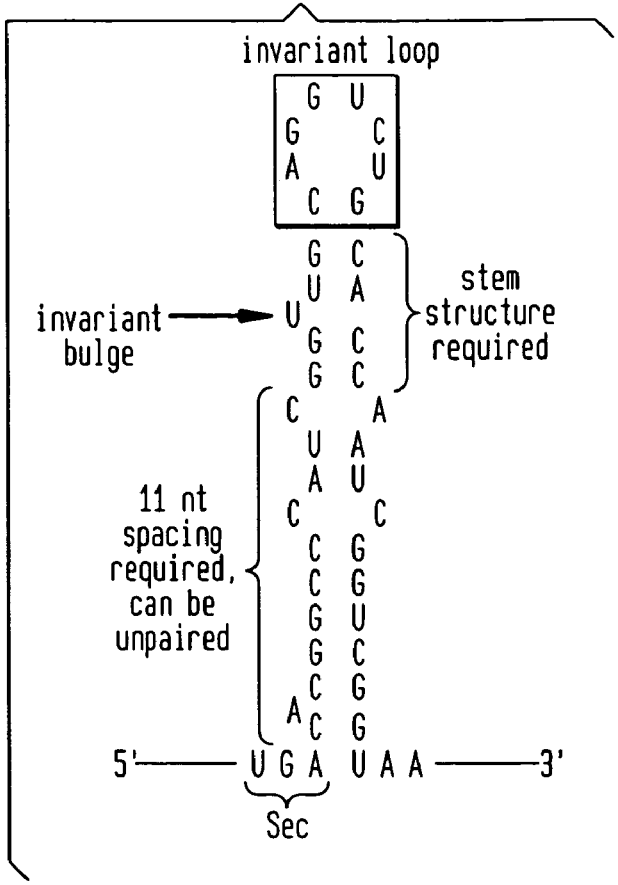
FIG. 2—The *E. coli* formate dehydrogenase (fdh) SECIS, with permissible mutations as reported in Heider, et al., *EMBO J.*, 11:3759–3766 (1992); Klug, et al., *Proc. Natl. Acad. Sci. USA* 94:6676–6681 (1997); Liu, et al., *Nucleic Acids Res.*, 26:896–902 (1998).

The mRNA requirements for *E. coli* Sec incorporation, summarized in FIG. 2, indicate that the minimal SECIS consists of a short hairpin sequence with fixed nucleotides, located exactly 11 bases downstream from the UGA stop codon. Considerable nucleotide flexibility is allowed in this intervening sequence, permitting incorporation of selenocysteine within a randomized stretch of amino acids.

The present invention comprises three components:

(a) an expression system for display of heterologous peptide and protein sequences on the surface of amplifiable genetic particles (bacteriophage, virus, polysome, cells, spores, etc.) as fusions to surface proteins;

(b) a UGA opal codon at the position in the displayed polypeptide where selenocysteine is to be incorporated; and (c) a minimal SECIS at the proper distance downstream from the UGA codon to direct Sec incorporation, incorporated so as not to interrupt the reading frame of the displayed polypeptide-surface protein fusion.

It is demonstrated in the Examples herein that selenopeptide libraries displayed on the surface of bacteriophage can be generated using an adaptation of standard phage display methods. The evidence for selenocysteine incorporation is described in Sandman, et al., *J. Am. Chem. Soc.,* 122: 960–961 (2000) and Sandman and Noren, *Nucleic Acids Res.* 28:755–761 (2000). Specifically, all of the TGAT library clones assumed to display exclusively selenopeptides formed plaques only in the presence of supplemental selenium. N-terminal sequencing of Maltose Binding Protein fusions revealed dehydroalanine, and not Trp, in several putative Sec-inserting clones. The chemical modification of the phage samples believed to contain Sec was consistent with selenium reactivity, with nucleophilic substitution readily occurring at acidic pH, where Cys is expected to be unreactive. Finally, the occurrence of clones encoding Cys proximal to the TGA codon also implicates Sec incorporation, since sulfide-selenide bridging would stabilize the otherwise unpaired Cys.

In accordance with the presentation, the molecular diversity of displayed peptides can now include twenty-one amino acids instead of the traditional twenty, but since the twenty-first amino acid can be specifically chemically modified, any desired functionality can be appended prior to each round of panning. Small libraries of appended functionalities may be screened by modifying the peptide libraries in separate and spatially addressable reaction vessels. Enzyme inhibitors may be identified by modifying Sec with substrate or transition state analogs and panning the resulting modified peptide libraries against enzymes. By tethering a known low-affinity inhibitor to a random peptide library, flanking residues which increase the overall affinity of the inhibitor-peptide chimera can be selected by standard phage panning methods. This concept of iterative ligand assembly has recently been demonstrated with small-molecule libraries (Maly, et al., *Proc. Natl. Acad. Sci. USA,* 97:2419–2424 (2000)), but the present invention extends this idea to take advantage of the vastly higher-complexity libraries allowed by surface display methods. The linkage of cytotoxic agents to the Sec residue, for example, may facilitate the discovery of peptide-drug complexes that are taken up into specific cell types. Particles simultaneously displaying enzyme libraries and substrate-derivatized selenopeptides may be screened for enzymes with enhanced activity or altered specificity. The covalent linkage of substrates to displayed peptides permits the rigorous reaction and selection conditions that might otherwise disrupt the noncovalent interactions utilized in recent examples of phage-mediated enzyme evolution. (Demartis, et al., *J. Mol. Biol.,* 286:617–633 (1999); Pedersen, et al., *Proc. Natl. Acad. Sci, USA* 95:10523–10528 (1998)).

The present invention also provides a useful tool for further study of the requirements for selenocysteine incorporation. By coupling plaque formation to selenocysteine incorporation it is possible to screen thousands of sequences at once, using a simple, nonradioactive visual readout that specifically indicates Sec incorporation rather than general opal suppression. Previous studies of prokaryotic SECIS requirements suggested that certain elements of the mRNA structure were essential, whereas others could be changed without affecting opal codon readthrough (Liu, et al., supra).

In accordance with the methods of the present invention, it was rapidly determined that the first nucleotide downstream of TGA strongly influences opal suppression in *E. coli,* with purines or CTG promoting a dual-pathway approach in which Trp insertion is always possible, and Sec insertion occurs if Se is available. TGA-pyrimidine sequences, on the other hand, only permit the inefficient cotranslational Sec insertion pathway, thereby occasionally allowing opal codon mutants to dominate a culture. The apparent stabilization of unpaired Cys residues by Sec overrides these rules, so that an adjacent unpaired Cys will strongly favor the Sec insertion pathway, regardless of the downstream nucleotide. This application has important implications for heterologous expression of mammalian selenoproteins in prokaryotic systems (Arner, et al., *J. Mol. Biol.* 292:1003–1016 (1999)): the present invention can be used to optimize the expression level of virtually any selenoprotein.

The present invention is further illustrated by the following Examples. These Examples are provided to aid in the understanding of the invention and are not construed to be a limitation thereof.

The references cited above and below are herein incorporated by reference.

Example I

Expression of Native *E. COLI* fdh Sequences as M13 pIII Fusion

As a control, the native *E. Coli* formate dehydrogenase (fdh) SECIS (FIG. 2, amino acid sequence Ser-Ala-Arg-Val-Sec-His-Gly-Pro (SEQ ID NO:28)) was cloned into M13KE, an M13 mp19 derivative designed with Acc65I and EagI sites for pentavalent N-terminal pIII expression (Zwick, et al., *Analytical Biochemistry,* 264:87–97 (1998)). The following oligonucleotides were synthesized by the phosphoramidite method by the Organic Synthesis Division of New England Biolabs, Inc. (Beverly, Mass.). Acc65I and EagI restriction sites are indicated in bold.

fdh SECIS control oligonucleotide:

5'-CATGTTTCGGCCGTACCGACCGATTGGT-GCAGACCTGCAACCGA TGGGCCGTGTCAGACAC-GAGCGCTAGAGTGAGAATAGAAAGGTACC CGGGCATG-3' (SEQ ID NO:29)

Duplex extension primer (New England Biolabs, (Beverly, Mass.) product #8101): 5'-CATGCCCGGGTACCTTTTC-TATTCTC-3' (SEQ ID NO:30)

The fdh SECIS control oligonucleotide was synthesized, gel-purified, and annealed to the duplex extension primer. The duplex was extended with dNTPs and Klenow fragment, digested with Acc65I and EagI, gel-purified and ligated into Acc65I/EagI digested phage cloning vector M13KE. The ligation products were electroporated into *E. Coli* ER2537 (F' lacI$^q$Δ(lacZ)M15 proA$^+$B$^+$/fhuA2 supE thiΔ(lac-proAB)Δ(hsdMS-mcrB) 5 and plated with 100 μL of a late log-phase ER2537 culture in 3 mL of agarose top on LB agar plates with 210 μM IPTG and 98 μM Xgal. The agarose top contained 10 g/L tryptone (Difco, Detroit, Mich.), 5 g/L yeast extract (Difco, Detroit, Mich.), 86 mM sodium chloride, 5 mM magnesium chloride, and 7 g/L agarose (American Bioanalytical, Natick, Mass.) supplemented with 2 μM sodium selenite. The M13KE vector carries the lacZα fragment, resulting in characteristic blue plaques when plated with an α-complementing strain on X-gal medium. After a 16 h 37° C. incubation, blue plaques were selected and the individual clones were amplified in early log-phase cultures of ER2537 supplemented with 2 µM sodium selenite. Sequencing templates were prepared by ethanol precipitation of phage DNA from 4 M sodium iodide (Wilson, *Biotechniques* 15:414–416, 418–420, and 420 (1993)). Phage clones were stored at 4° C. in a 150 mM Tris pH 7.4, 50 mM sodium chloride, 100 µM DTT buffer with 0.02% sodium azide. Automated DNA sequencing was performed on a PE-ABD 377 or 373 instrument using Dye-Deoxy™ terminator chemistry (PE Applied Biosystems, Foster City, Calif.) with the −96 gIII sequencing primer (New England Biolabs, Inc. (Beverly, Mass.) product #1259, 5'-CCCTCATAGTTAGCGTAACG-3' (SEQ ID NO:31)), and yielded the expected sequence (designated Sec-1).

pMal-pIII Fusion Protein Expression.

Figure 3A:
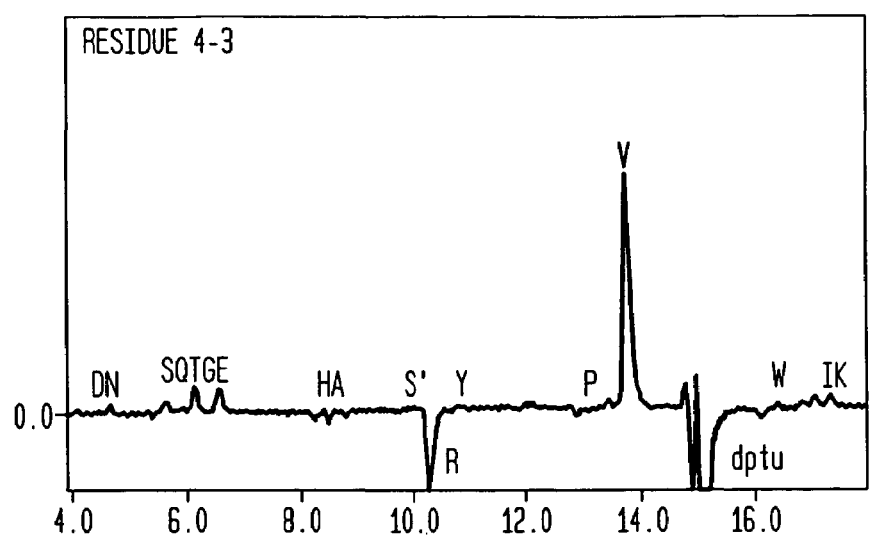
FIG. 3A—Cycle 3 subtracted from cycle 4.
Figure 3B:
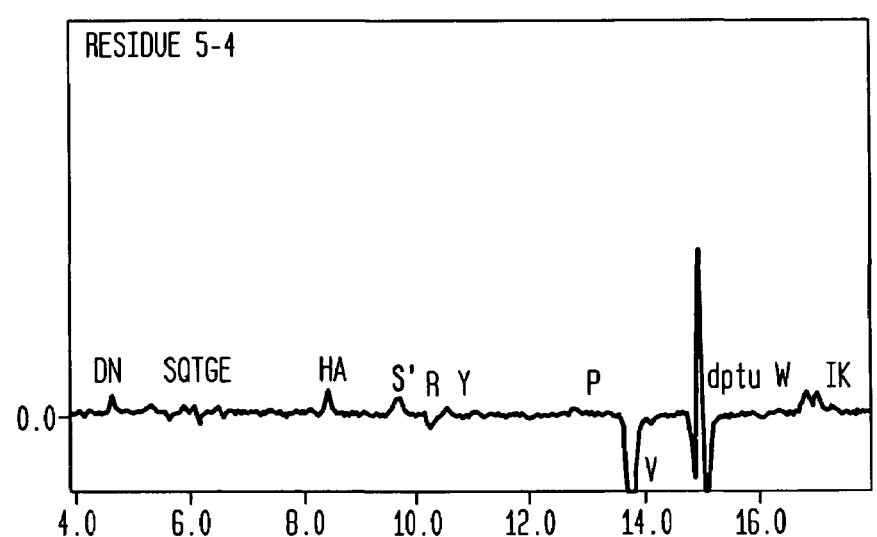
FIG. 3B—Cycle 4 subtracted from cycle 5.
Figure 3C:
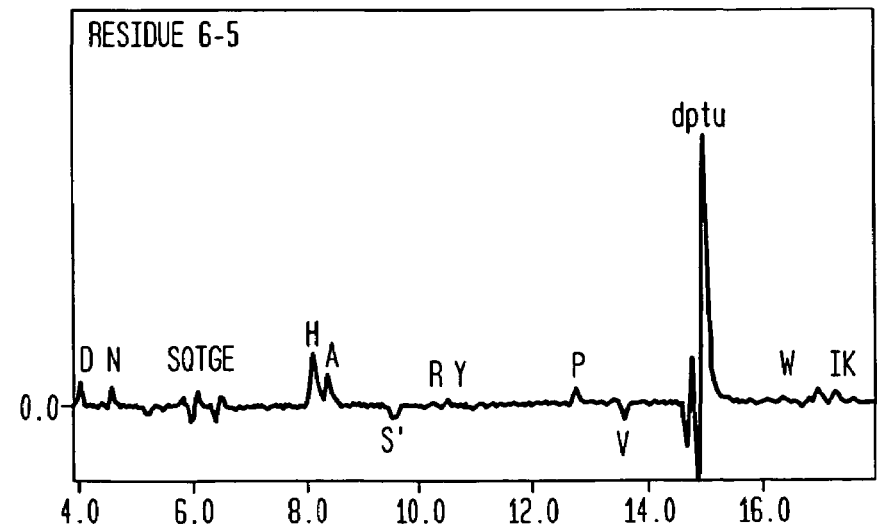
FIG. 3C-*Cycle* 5 subtracted from cycle 6. S=serine; S'=dehydroalanine (expected acid breakdown product of Sec).

In order to obtain sufficient quantity of material for confirmation of Sec incorporation by N-terminal protein sequencing, the pMal-pIII shuttle vector (Zwick, et al., supra) was employed to overexpress and purify the Sec-1 peptide sequence as a fusion to the N-terminus of maltose binding protein (MBP). The resulting construct contains a pIII leader sequence to direct the fusion to the periplasm, resulting in the N-terminus of the MBP fusion being identical to that of the phage-displayed fdh sequence. The digested and gel-purified fdh SECIS insert was ligated into Acc65I/EagI digested pMal-pIII protein expression vector. The ligation products were electroporated into ER2537, plated on LB with 100 µg/mL ampicillin, and analyzed by restriction mapping and automated DNA sequencing. The pMal-pIII fusion proteins were expressed in ER2537 and purified as previously described (Zwick, et al., supra). For N-terminal protein sequencing, proteins were subjected to electrophoresis and electroblotted according to the procedure of Matsudaira (Matsudaira, *J. Biol. Chem.*, 262:10035–10038 (1987)), with modifications as previously described (Looney, et al., *Gene* 80:193–208 (1989); Waite-Rees, et al., *J. Bacteriol.* 173:5207–5219 (1991)). The membrane was stained with Coomassie blue R-250 and the protein band of approximately 46 kDa was excised and subjected to sequential Edman degradation on a PE-Biosystems (Foster City, Calif.) 494A Protein/Peptide Sequencer using standard gas-phase cycles (Waite-Rees, supra). The results (FIG. 3) showed the expected Sec-1 N-terminus, SARVXHGPSV (SEQ ID NO:32), with X assumed to be Sec. The acid breakdown product of a Sec residue, generated by acid-catalyzed β-elimination, should be the same as Cys or Ser residues in that all produce dehydroalanine (S'). The DTT adduct of the dehydroalanine PTH was observed at the position corresponding to the TGA codon (cycle 5). Ser also produces this adduct, but cycles 1 and 9, and not cycle 5, also showed a parent Ser peak. No significant amount of Trp-PTH (<200 fmol) was observed in this cycle, eliminating the possibility of endogenous Trp-inserting opal suppression.

Example II

Construction and Characterization of TGAN And TGAT Libraries

Figure 4:
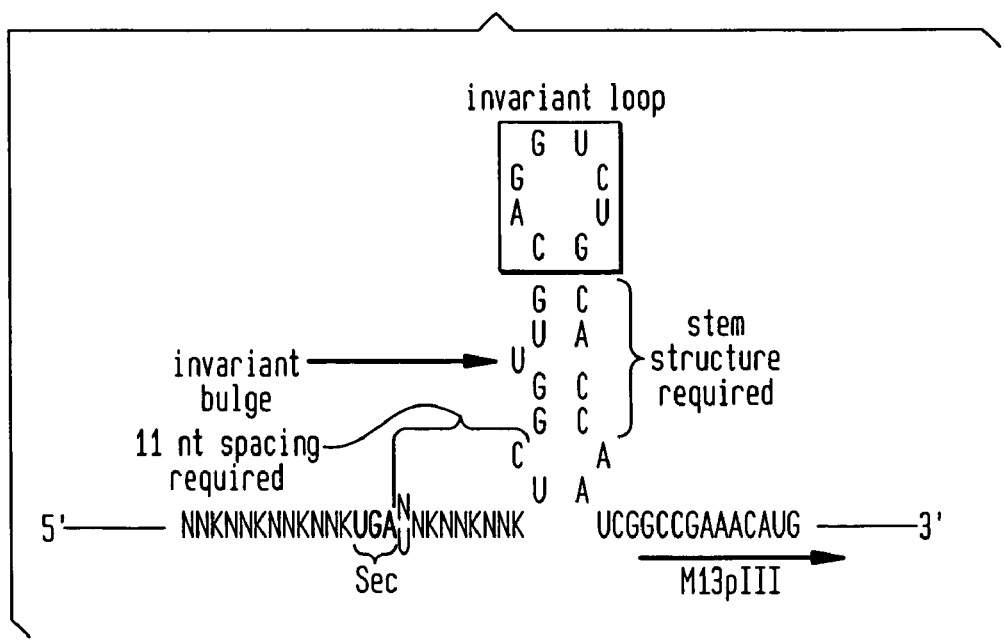
FIG. 4—The randomized SECIS library inserts expressed as M13 pIII fusions. N=A, G, C or U. K=G or U. Permissible mutations are based on the *E. coli* formate dehydrogenase (fdh) SECIS as reported in Liu, et al., supra. The position immediately downstream from the UGA codon is fully randomized in the TGAN library, and is fixed as U in the TGAT library. (SEQ ID NO:1)

Based on the reported minimal SECIS requirements (FIG. 2) (Liu, et al., supra), a library consisting of the SECIS element with four upstream and three downstream randomized codons, and a minimal mRNA SECIS (TGAN library, FIG. 4), was prepared using the same cloning strategy described in Example I. The TGAN library oligo sequence was as follows, with Acc65I and EagI restriction sites in bold; M=A or C; N=A, C, T or G.

5'-CATGTTTCGGCCGATTGGTGCAGACCTGCAACCGAMNNMNNM
NNTCAMNNMNNMNNMNNAGAGTGAGAATAGAAAGGTACCCGGG-3'
(SEQ ID NO:33)

After duplex extension and restriction digestion, the resulting insert was ligated into M13KE, an M13mp19 derivative designed with Acc65I and EagI sites for pentavalent N-terminal pIII expression (Zwick, et al., supra). This vector also carries the lacZα fragment, resulting in characteristic blue plaques when plated with an α-complementing strain on X-gal medium. The sequences of selected clones are shown in FIG. 9. Although the immediate downstream nucleotide was fully randomized in the TGAN library insert, the majority (74%) of the resulting phage clones possessed a downstream purine. One-third of the displayed peptides in the TGAN library possessed an unpaired Cys residue, which corresponds to 4.8% of the total randomized amino acids. Based on random codon usage, the calculated expected frequency for Cys is 3.1%, whereas the typically observed Cys frequency using this phage display system is less than 0.5%. Because M13 proteins are exported to the periplasm, the pairing of the eight Cys residues in M13 pIII into four disulfide bonds (Holliger and Riechmann, *Structure* 5:265–275 (1997)) could be disrupted by a single unpaired Cys within the displayed peptide. This phenomenon would likely not be observed with a cytoplasmically-expressed peptide library.

A second library (TGAT library, FIG. 4) was also constructed in which the nucleotide immediately downstream from the UGA codon was fixed as U (T in the DNA) in order to prevent endogenous tryptophan-inserting opal suppression, which is enhanced by downstream purines and the trinucleotide CUG (Miller and Albertini, *J. Mol. Biol.* 164:59–71 (1983)). The TGAT library was constructed as described above using the library oligonucleotide 5'-5'-CATGTTTCGGCC GATTGGTGCAGACCTGCAAC-CGAMNNMNNMNATCAMNNMNNMNN MNNA-GAGTGAGAATAGAAAGGTACCCGGG-3' (SEQ ID NO:34), where the EagI and Acc65I sites are indicated in bold (M=A or C; N=A, C, T or G). The electroporation and plating of the library ligation products resulted in small plaques, with about ten times more plaques forming in the presence of 2 µM supplemental sodium selenite as compared to unsupplemented medium. Individual plaques were amplified for further analysis, with representative sequences shown in FIG. 10. The growth of all of the TGA-containing clones was strictly selenium-dependent, with plaques appearing only in the presence of 1–2 µM supplemental sodium selenite. M13KE phage growth, by contrast, was selenium-independent over a range of 0–4.5 µM supplemental sodium selenite. As with the TGAN library, single Cys residues occurred in the TGAT library at a higher than normal frequency of 4.3% of all random amino acids. The TGAT library also had occasional (<10% frequency) mutations within the opal codon, such as the point mutation in clone TGAT-13 (FIG. 10), which converted the TGA opal codon to the CGA Arg codon.

Selenium Dependency of Phage Growth.

Figure 5:
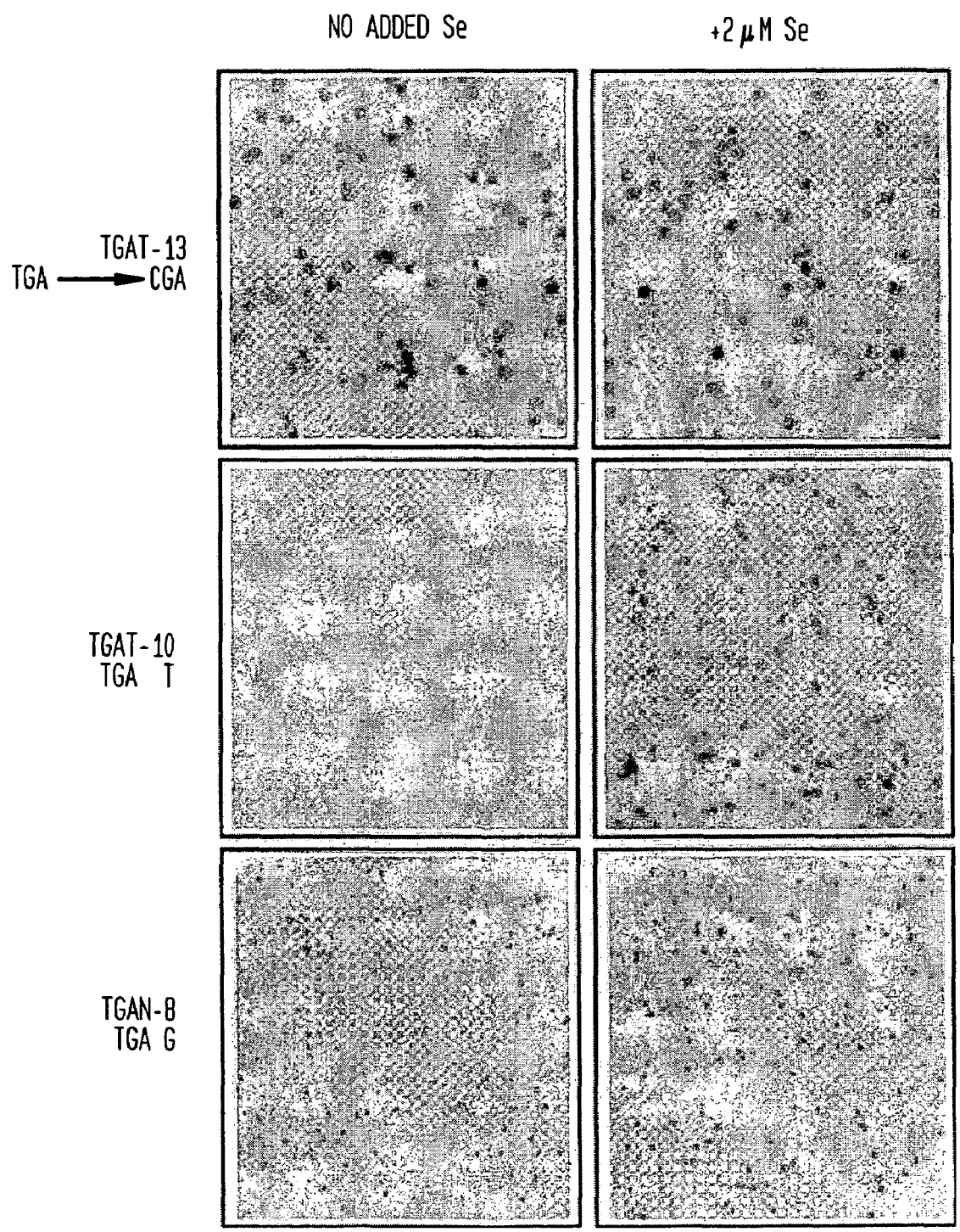
FIG. 5—Plating results showing Se-dependent and independent growth of phage clones TGAT-13, TGAT-10 and TGAN-8 (sequences in FIGS. 9 and 10). Left column: no supplemental Se in plating medium. Right column: 2 µM sodium selenite added to plating medium.

To assess the selenium dependency of phage production, phage samples were plated in media with or without 2 µM supplemental sodium selenite. Individual phage clones were diluted in LB and combined with 200 µL of a late log-phase ER2537 or ER2738 culture. After a 5 min incubation at room temperature, the bacteria and phage were combined with 3 mL of agarose top, with or without supplemental 2 µM sodium selenite, and plated on LB agar plates with IPTG and Xgal. After a 16 h 37° C. incubation the plates were inspected for the presence of blue plaques. Typical results are illustrated in FIG. 5 and summarized in the third column of FIG. 9 and FIG. 10. Selenium-independent phage clones, such as TGAT-13 and TGAN-8, produced plaques of equal count and size regardless of the media selenium concentration. In contrast, clone TGAT-10 and other Se-dependent phage only produced plaques in Se-supplemented medium. To further quantitate the strict selenium dependence of phage growth, Clone TGAT-6 (ASPTSecFKP) was plated with varying concentrations of supplemental sodium selenite in the medium. FIG. 6 shows that the number and diameter of visible Clone 6 plaques increased in a selenium-dependent fashion from 0–3.2 µM sodium selenite, with half-maximal plaque diameter at ~0.4 µM selenite.

All of the clones with an immediate downstream purine grew in a Se-independent manner, with the exception of those containing a single Cys codon within the displayed peptide sequence, e.g., TGAN-7, FIG. 9. All of the clones with an opal codon immediately followed by a pyrimidine grew in a Se-dependent manner, with the exception of clone TGAN-10, which had a downstream CTG codon. All of the clones with mutated opal codons, such as TGAT-13, were Se-independent, as was M13KE phage without insert.

N-Terminal Sequencing.

To further analyze the displayed peptides, the pMal-pIII shuttle vector was employed (Zwick, et al., supra). This vector allows inserts from M13KE to be expressed as fusions to the N-terminus of maltose binding protein (MBP), with a pIII leader sequence to direct the fusions to the periplasm. The TGAN-1 peptide, in which the UGA codon is followed by an A, was overexpressed and purified using this system. N-terminal sequencing revealed mostly (>90%) Trp incorporation at the TGA site, as expected from endogenous Trp-inserting opal suppression favored in this sequence context (Miller and Albertini, supra). This is fully consistent with the observed selenium independence of this clone. By contrast, the results of sequencing an MBP fusion with the selenium-dependent clone TGAT-12 were comparable to data obtained with the Sec-1 *E. coli* fdh SECIS insert (FIG. 3), consistent with Sec and not Trp insertion.

Example III

Chemical Modification of Selenopeptide Libraries

To rule out the possibility of Cys incorporation at the TGA codon, and to demonstrate specific chemical modification of the Sec residue in a displayed peptide, the chemical reactivity of the fdh control phage clone Sec-1 (SARV-Sec-HGP) was compared to that of clone Cys-1 (SARVLCNH (SEQ ID NO:35)), which contains a single unpaired cysteine residue. Phage samples were treated with iodoacetyl-LC-biotin (I-Bt, Pierce), an electrophilic reagent which should specifically target thiol or selenol groups with the enzyme cofactor biotin. Phage ($10^{10}$ pfu) in 150 mM sodium chloride, 50 mM glycine-HCl (pH 2.5) were combined with 50 µM iodoacetyl-LC-biotin in dimethylformamide (5% v/v) and incubated in the dark at room temperature for 10 min. The reactions were quenched by the addition of SDS gel loading buffer with 42 mM DTT, and samples were promptly denatured at 100° C. for 5 min and loaded on a 10–20% SDS-polyacrylamide gel. Immunoblotting was performed according to standard procedures, and the blots were probed with HRP-conjugated anti-biotin antibody (1:1000 dilution) or a mouse monoclonal anti-pIII antibody (Bio 101; 1:500 dilution) followed by an HRP-conjugated anti-mouse antibody. The blots were developed using the Phototope® Chemiluminescence kit (New England Biolabs, Inc., Beverly, Mass.).

Figure 7B:
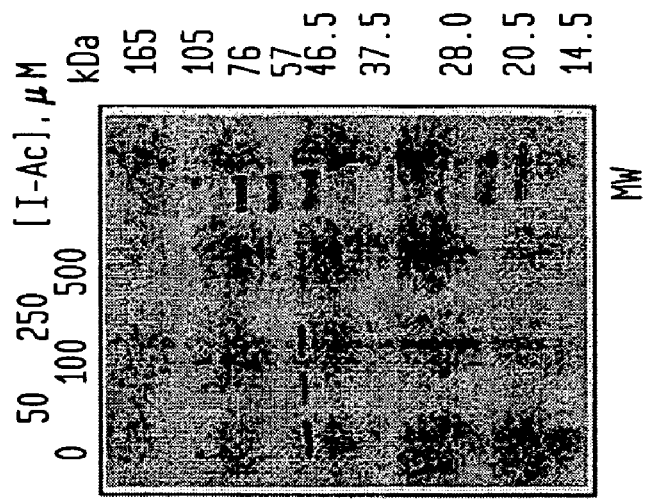
FIG. 7B—Sec-1 samples, treated with the indicated concentration of iodoacetamide for 1 h at room temperature, followed by 50 µM I-Bt for 20 min.
Figure 7A:
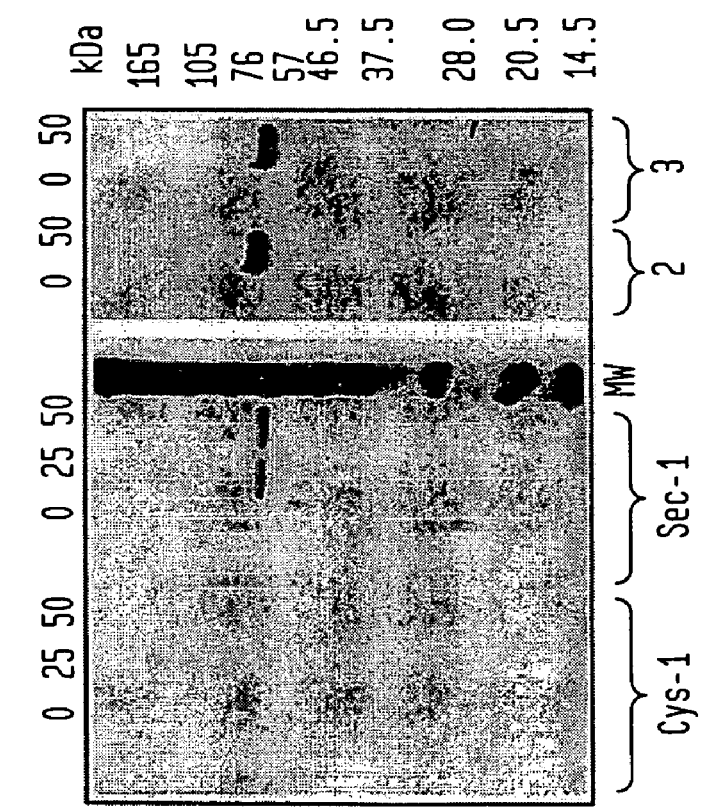
FIG. 7A—Phage samples (peptide sequences in FIG. 9), treated with I-Bt for 30 min.

FIG. 7A shows the results of immunoblotting of the products. At both pH 2.5 and pH 8, the biotinylation was highly specific for the Sec residue. Biotinylation of Cys-1 was enhanced at pH 8, although the reaction remained highly selective (>10:1) for Sec. The biotinylation experiments confirm that, at acidic pH, the reactivity of a Sec residue in a pIII fusion greatly exceeds that of the eight paired Cys residues (Holliger and Riechmann, supra) in M13 pIII or of an unpaired Cys residue in the displayed peptide.

Presumably because of the stability of sulfide-selenide cross-links, the selenopeptide library contained clones with a single Cys residue at a much higher incidence than is normally seen in pIII libraries constructed in the M13KE system. To determine whether the putative sulfide-selenide bridging inhibited Sec reactivity, phage clones TGAT-2 and TGAT-3 were modified with I-Bt; immunoblotting revealed that both samples were biotinylated to a similar extent as Sec-1 (FIG. 7A). This result suggests that the sulfide-selenide cross-link is sufficiently reversible to allow trapping of the free selenide with an excess of electrophile.

To estimate the efficiency of chemical modification, Sec-1 phage was modified with iodoacetamide (I-Ac), and the remaining unmodified phage was then reacted with I-Bt and detected by immunoblotting (FIG. 7B). Treatment for 1 h with 250 µM I-Ac at pH 2.5 was sufficient to block the biotinylation reaction. Because the electrophilicities of I-Ac and I-Bt are essentially identical, this result suggests that modification with I-Bt under these conditions would go to completion. To assess the infectivity of the modified phage, the Sec-1 clone was treated for 1 h at room temperature at pH 5.2 with I-Ac or I-Bt. After quenching with two equivalents of β-mercaptoethanol to scavenge any unreacted I-X electrophile, the samples were diluted and plated, with no significant effect on the resulting plaque counts.

Example IV

Identification of SECIS Requirements

The mRNA requirements for *E. coli* Sec incorporation were previously determined by cloning the *E. coli* formate dehydrogenase gene (fdh) with non-native SECIS variants upstream of a β-galactosidase reporter gene, and then measuring either $^{75}$Se incorporation by SDS-PAGE or β-galactosidase expression by a calorimetric assay (Chen, et al., *J. Biological Chemistry*, 268:23128–23131 (1993); Heider, et al., *EMBO J.*, 11:3759–3766 (1992); Liu, et al., supra; Zinoni, et al., *Proc. Natl. Acad. Sci. USA* 84:3156–3160 (1990). Although reporter gene expression is the more quantitative of the two approaches, it is a measure of TGA suppression but not necessarily Sec incorporation. Many *E. coli* strains possess endogenous opal suppression activity resulting in tryptophan (Trp) incorporation (Miller and Albertini, supra), suggesting that a portion of the reporter gene expression could have been independent of Sec incorporation.

The coupled phage display assay which comprises the present invention was utilized to further investigate the *E. Coli* SECIS requirements (Sandman and Noren, supra). The native M13 proteins do not contain Sec (Ebright, et al., *Gene* 114:81–83 (1992); van Wezenbeek and Schoenmakers, supra), and M13 phage infectivity requires expression of the coat protein pIII (Holliger and Riechmann, supra). The fusion of putative selenopeptides to the N-terminus of pIII therefore should couple phage plaque formation to opal suppression. Because of the relatively high level of protein synthesis required for plaque formation, it was anticipated that selenium-supplemented media would be required for selenopeptide phage display. Putative selenopeptide-pIII fusions could thus be identified based on the selenium dependence of plaque formation, and this in vivo method could be used to identify critical SECIS elements from phage libraries. The utility of in vitro combinatorial methods was previously shown when RNA aptamer libraries were screened for SelB binding (Klug, et al., supra). The SECIS $U_{17}$ bulge, noted in FIG. 2, was found to be required for SelB binding, which in turn is necessary for Sec incorporation. Whereas the aptamer method only revealed in vitro binding events, the phage display method provides a direct readout of prokaryotic Sec incorporation requirements in vivo.

In addition to selenium dependency of phage formation, Sec incorporation can also be assessed by modifying phage samples with readily detectable reagents as described in Example III. The pKa of Sec is 5.2, compared to 8.1 for cysteine (Cys), so that at pH 6–7, nucleophilic substitution reactions can specifically alkylate a Sec residue without modifying neighboring Cys residues (Gorlatov and Stadtman, supra). Example III describes a method to assay phage for selenopeptide display by treatment with an electrophilic iodoacetamido-biotin reagent, followed by detection of biotinylated phage with an anti-biotin antibody. Because the reactivity of Sec is unique from that of any other naturally occurring amino acid side chain, chemical reactivity is a more specific indicator of Sec than opal suppression.

Effect of Media Selenite on Selenocysteine Incorporation.

To explore the effect of sequence context on opal suppression, individual phage clones were amplified in media with or without supplemental 2 μM selenite. The resulting phage was quantitated by plating diluted samples, and the phage DNA was sequenced. As a test of Sec incorporation in the displayed peptides, phage clones were treated with iodoacetyl-LC-biotin (I-Bt) as in Example III, and the level of biotinylation was assessed by immunoblotting. As controls, M13KE phage and clones displaying a single unpaired Cys (Cys-1, displayed peptide SARVLCNH (SEQ ID NO:35) or Sec (Sec-1, displayed peptide SARVSecHGP, corresponding to the *E. coli* fdh SECIS) were used.

Figure 8A:
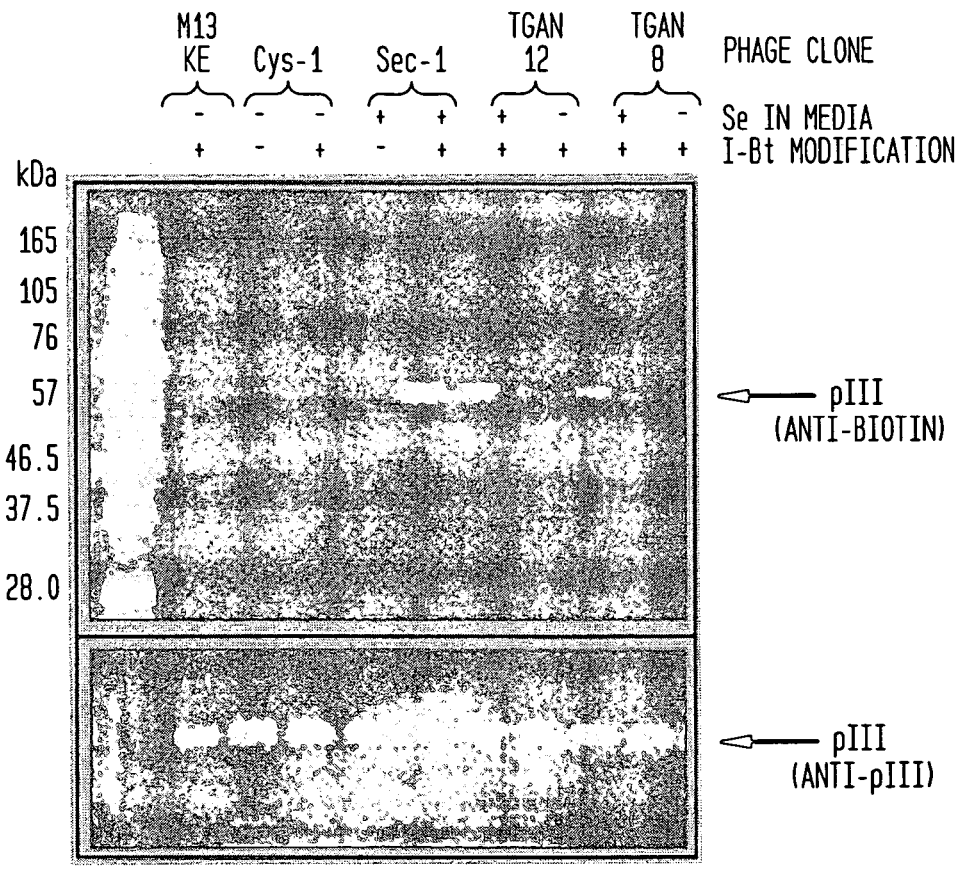
FIG. 8—Immunoblots showing specific chemical modification of phage displaying selenopeptides. Individual library clones from the TGAN library (A) or TGAT library (B) were amplified with or without 2 µM supplemental sodium selenite as indicated. Phage were modified as described in Example III. *Amplification of clone TGAT-1 in unsupplemented medium resulted in a TGA→TGG point mutation.
Figure 8B:
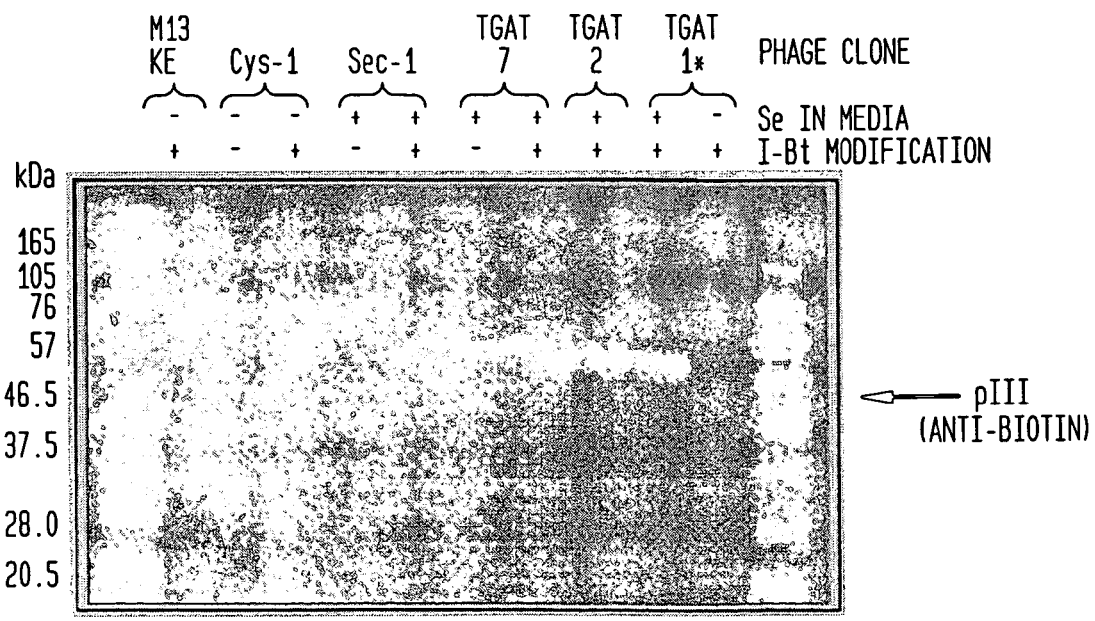

Clones TGAN-12 and TGAN-8, both of which had a downstream purine, produced equivalent levels of phage in supplemented and unsupplemented media. Growth of both clones in media with selenite substantially enhanced the reactivity of the resulting phage (FIG. 8A). Production of TGAN-7, which had a downstream purine and a single Cys, was enhanced 50-fold by supplemental Se. Clones with a downstream pyrimidine and a single Cys in the displayed peptide, such as TGAT-7 and TGAT-2, produced 1000-fold less phage without supplemental Se. The phage produced with supplemental Se from these clones had reactivity equal to that of the control Sec-1 phage (FIG. 8B). Clones such as TGAT-1, which possessed a downstream pyrimidine and no Cys in the displayed peptide, either had very low phage production in the absence of supplemental Se, or produced phage with opal codon mutations. FIG. 8B shows that clone TGAT-1 was reactive when amplified with Se; the TGA→TGG mutant resulting from amplification without Se was unreactive. Occasionally, TGAT clones also developed opal codon point mutations during amplification with supplemental Se.

The expression of randomized SECIS elements as N-terminal fusions to M13 pIII couples phage production to opal suppression, providing a combinatorial approach to understanding cotranslational Sec insertion. If a sequence fails to produce phage, then it is assumed that there is no opal suppression. If phage is produced in a Se-dependent manner, the opal suppression is presumed to be Sec-inserting. Se-independent phage production can result from Trp insertion or from mutations within the opal codon.

In addition to the principal requirement for Sec incorporation, the opal codon with a downstream SECIS, the invention demonstrates that the presence of a single Cys residue within a peptide displayed on M13 pIII is an important factor in Sec insertion. The occurrence of single Cys residues in selenopeptides was over 4%, higher than both the normally observed (<0.5%) and predicted (3.1%) frequencies for similar displayed peptide libraries. Moreover, library clones containing a single Cys residue possessed opal codon mutations with <1% frequency compared to almost 10% for the entire TGAT library. These effects presumably resulted from seleno-sulfide cross-linking, which would stabilize both the Cys and Sec residues in the M13 display system, where the coat protein pIII folds in the periplasm. Because it was possible to obtain and amplify many stable library clones containing an unpaired Sec but not a Cys, it appears that single Sec residues are somewhat more stable than unpaired Cys residues.

Among sequences that did not contain a single Cys residue, the nucleotide immediately downstream was a critical factor in determining whether Sec or Trp insertion occurred. The TGA-purine clones replicated with comparable phage yield and sequence fidelity regardless of the media Se concentration, suggesting that Sec insertion was not the major pathway. Purines in the first downstream position have previously been shown to enhance Trp-inserting opal suppression by endogenous tRNA$^{Trp}$ (Miller and Albertini, supra). Notably, the TGA CTG sequence present in the Se-independent clone TGAN-10 has also been shown to strongly promote Trp insertion (Miller and Albertini, supra). It was recently demonstrated that a downstream SECIS element enhanced opal suppression, presumably by Trp, even in the absence of functional SelB or SelC, possibly by interfering with RF2-dependent termination or by stabilizing the message (Suppmann, et al., *EMBO J.*, 18:2284–2293 (1999)). Although the combination of the immediate downstream purine/CTG and the mRNA SECIS appeared to drive the Trp insertion pathway, it did not prohibit Sec insertion. Amplification of the TGA-purine clones in Se-supplemented media permitted Sec insertion, with phage reactivity comparable to that of fully Se-dependent clones.

Clones with an immediate downstream pyrimidine, except for CTG (TGAN-10), appeared to utilize primarily the Sec insertion opal suppression pathway; they required supplemental Se in order to produce functional phage, which was reactive with I-Bt. No other opal suppression pathway was implicated, since amplification in unsupplemented media resulted in either very low phage production or opal codon mutations. The occasional tendency of these clones to acquire opal mutations during Se-supplemented amplification was consistent with the recent finding that *E. coli* Sec insertion is only about 5% efficient (Suppmann, et al., supra). A spontaneous mutation in the opal codon would result in more efficient phage production, so that mutants would rapidly dominate the log-phase bacterial culture.

It has been shown (Poole, et al., *EMBO J.* 14:151–158 (1995)) that the nucleotide immediately downstream of the opal codon influences translational termination efficiency in E. coli, with an overall order of U>G>A>C. It was proposed that the recoding event of Sec insertion is favorable at the UGAC in E. coli fdh because RF2 binding is unfavorable in this context. The present data demonstrates that any nucleotide in the downstream position is capable of directing Sec insertion, and indeed, UGAU and UGAC are equally proficient. This suggests that the pathway leading to Sec insertion is independent of any effect of the immediate downstream nucleotide on RF2 binding.

All of the factors discussed above contribute to the observed preference for immediate downstream purines in the TGAN library. The downstream purine, followed by a SECIS, permitted maximal utilization of the endogenous opal suppression pathway without preventing cotranslational Sec insertion. This dual-pathway strategy effectively maximizes phage production. The fixed downstream pyrimidine (TGAT) library clones strongly favor the Sec insertion pathway, presumably resulting in more homogeneous displayed peptides. The cost of this homogeneity, however, is the likelihood of selection for adventitious mutations. These issues should be considered in cloning strategies for the bacterial expression of Sec-containing peptides and proteins.

Example V

A Selenosulfide-Constrained Peptide Library

Disulfide-constrained peptide libraries have been widely used for the discovery of high-affinity ligands for a number of targets (Giebel, et al., *Biochemistry*, 34:15430–15435 (1995); McLafferty, et al., *Gene* 128:29–36 (1993); O'Neil, et al., *Proteins* 14:509–515 (1992)). Flanking the randomized sequence with cysteine residues results in spontaneous oxidation of the thiol groups in aqueous buffer to form a disulfide crosslink. This results in the display of each peptide in the library as a disulfide-constrained loop, improving the free energy of binding by lowering the unfavorable entropic change associated with binding a free peptide to a target. Additionally, libraries of this type have proven useful in the identification of structural epitopes for antibodies (Luzzago, et al., *Gene* 128:51–57 (1993), and mimotopes (McConnell, et al., *Gene* 151:115–118 (1994)).

Figure 11:
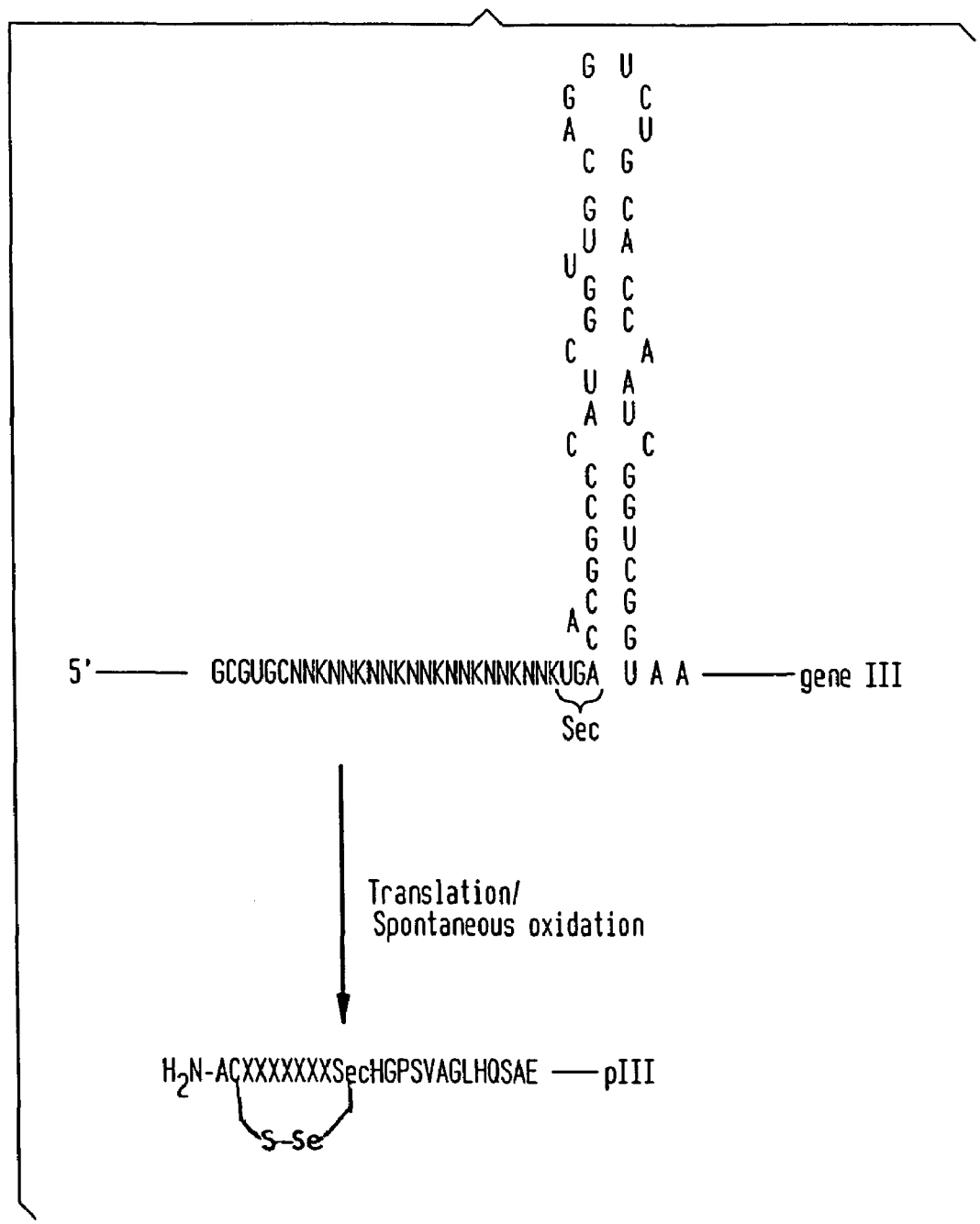
FIG. 11—Schematic of selenosulfide-constrained heptapeptide library displayed as an N-terminal fusion to pIII of M13. The randomized sequence is flanked by an upstream cysteine (C) residue and a downstream selenocysteine (Sec) residue, which spontaneously oxidize to yield a redox-stable selenosulfide cross-link. Selenocysteine is encoded by the opal codon UAG with a SECIS immediately downstream. Each randomized residue is encoded by NNK, where N is an equimolar mixture of G, A, U, C; and K is equimolar U and G. (SEQ ID NO:40 and SEQ ID NO:41)

A drawback of disulfide-constrained libraries is that the disulfide crosslink is not stable under mildly reducing conditions, as are required by redox-sensitive protein targets such as bacterial cytoplasmic proteins. Under conditions where these targets would be expected to be stable, e.g., 10 mM dithiothreitol (DTT), a cysteine flanked peptide library would be linear and unstructured, rather than constrained. A solution to this problem is to replace one of the cysteines with selenocysteine (Sec), resulting in a spontaneous selenosulfide (Se-S) crosslink which would be stable under mildly reducing conditions. Using the present invention as embodied in Examples I–III described herein, a Sec encoding UAG opal codon, with an appropriately spaced SECIS element, can be incorporated on one side of a randomized segment of codons. A cysteine codon (UGU or UGC) is introduced on the other side, resulting the in the randomized segment being structurally constrained by a redox-stable selenosulfide crosslink (FIG. 11).

As a demonstration of this technique a known ligand-target pair was chosen in which a disulfide constraint was previously shown to enhance binding of the ligand to the target. By flanking the ligand sequence with a pair of cysteines, or cysteine and selenocysteine, it was expected that both would bind the target well under nonreducing conditions, but only the selenosulfide-constrained sequence would bind well under reducing conditions. The ligand-target pair chosen was the sequence Cys-HPQGPP-Cys, (SEQ ID NO:36) which was demonstrated to bind streptavidin with 65-fold higher affinity than the linear sequence Ser-HPQGPP-Ser (SEQ ID NO:36) (Giebel, et al., supra).

The following oligonucleotides were synthesized, purified, annealed, extended and ligated into M13KE as described in Example I (Eag I and Acc65 I sites underlined):

```
Ser-Ser:
5'-CATGTTTCGGCCGATTGATGAAGCCCAGCCAC    (SEQ ID NO:37)

GCTTGGGCCGTGGCTCGGTGGACCTTGCGGATGGC

TTTCCGCAGAGTGAGAATAGAAAGGTACCCGGG-3'

Cys-Cys:
5'-CATGTTTCGGCCGATTGATGAAGCCCAGCCAC    (SEQ ID NO:38)

GCTTGGGCCGTGGCACGGTGGACCTTGCGGATGGC

ATTCCGCAGAGTGAGAATAGAAAGGTACCCGGG-3'

Cys-Sec:
5'-CATGTTTCGGCCGATTGGTGCAGACCTGCAAC    (SEQ ID NO:39)

CGATGGGCCGTGTCACGGTGGACCTTGCGGATGGC

ATTCCGCAGAGTGAGAATAGAAAGGTACCCGGG-3'
```

All three inserts encode the same sequence HPQGPP (SEQ ID NO:36), but flanked by Ser—Ser, Cys—Cys and Cys-Sec as indicated. The Cys-Sec insert has the E. coli fdh SECIS immediately downstream of the UGA opal codon, while the other inserts have the same amino acid sequence encoded by the SECIS but a different nucleotide sequence, abolishing any selenocysteine-directing activity. To enhance selenocysteine incorporation, media contained 2 μM sodium selenite in all plating and amplification steps for the Cys-Sec construct, but not the others.

Following electroporation into E. coli ER2738, plaques were picked and amplified in 20 ml early-log cultures of ER2738 for 5 hours at 37° C. Cells were removed by centrifugation and phage recovered from the supernatant by overnight precipitation with ⅙ volume 20% polyethylene glycol 8000 in 2.5 M NaCl at 4° C. Following centrifugation and reprecipitation, phage were suspended in 100 μl Tris-buffered saline (TBS), pH 8 and titered for plaque forming units. DNA sequencing indicated that the phage were displaying the correct sequences, with the exception of the Cys-Sec phage, which carried a point mutation which resulted in the displayed sequence being Cys-HPQGPT-Sec (SEQ ID NO:42), rather than Cys-HPQGPP-Sec.

Binding to streptavidin was assayed by enzyme-linked immunosorbant assay (ELISA), using diluted phage as the primary detection and anti-M13 antibody as secondary. Polystyrene plates were coated overnight with streptavidin (Prozyme, San Leandro, Calif.) at a concentration of 100 μg/ml in 0.1 M bicarbonate buffer, pH 8.6. Plates were blocked with 1 mg/ml bovine serum albumen in TBS and washed with TBS containing 0.05% Tween-20 (TBST). Phage were diluted in TBS either containing 10 mM dithiothreitol (DTT) or not containing DTT, and applied to the blocked, streptavidin-coated wells. After a 2 h incubation at 20° C., plates were washed extensively with TBST and bound phage were detected with anti-M13 antibody conjugated to horseradish peroxidase (Amersham-Pharmacia, Piscataway, NJ), following the instructions provided by the manufacturer.

Figure 12A:
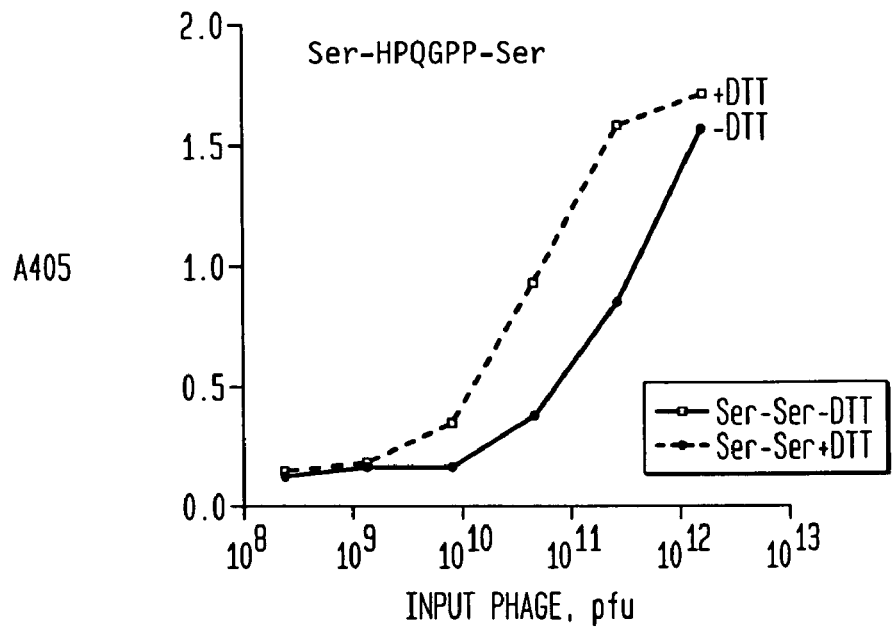
FIGS. 12A, 12B and 12C—Phage ELISA showing binding of the indicated linear (Ser—Ser) (FIG. 12A), disulfide constrained (Cys—Cys) (FIG. 12B) and selenosulfide constrained (Cys-Sec) (FIG. 12C) sequences to streptavidin, in the presence and absence of 10 mM dithiothreitol (DTT). Purified phage displaying the indicated constrained or unconstrained peptide sequence were added in the indicated amounts (pfu, plaque forming units). Following washing, bound phage were detected with anti-M13 antibody conjugated to horseradish peroxidase. Following development with $ABTS/H_2O_2$ in citrate buffer, plates were read in an ELISA plate reader at 405 nm.
Figure 12B:
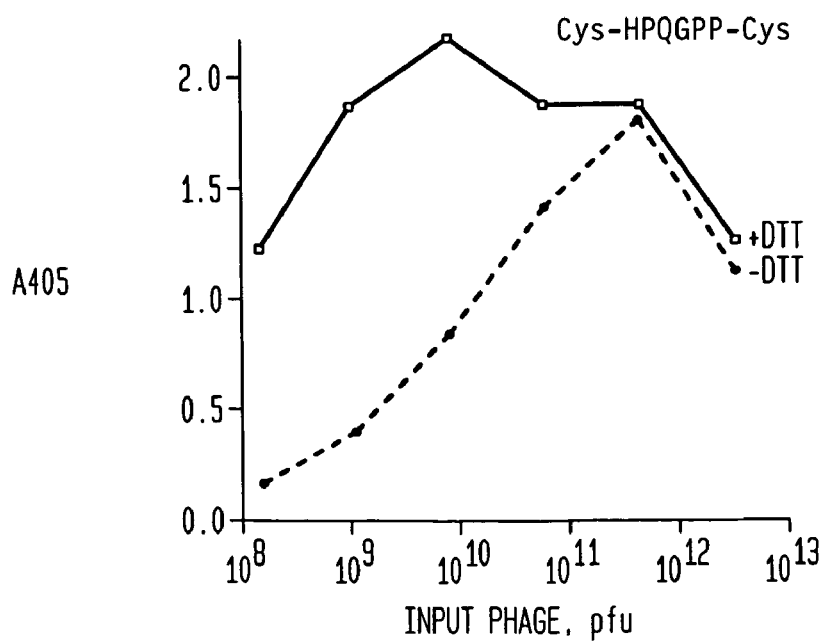
Figure 12C:
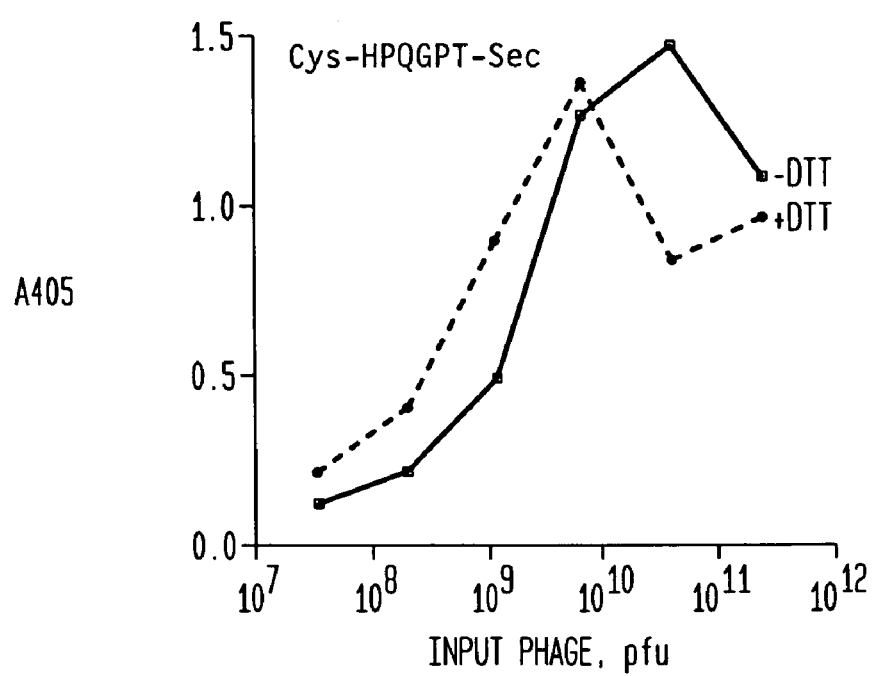

The results (FIG. 12) clearly show that binding of the Cys—Cys sequence to streptavidin is reduced by at least two orders of magnitude in the presence of 10 mM DTT. In contrast, both the linear (Ser—Ser) and the selenosulfide-constrained (Cys-Sec) sequences bind more tightly in the presence of DTT, possibly due to partial unfolding of pIII, which has 4 disulfide bonds, which may increase target accessibility of the displayed peptide. Importantly, the Cys-Sec sequence binds 2 orders of magnitude more tightly than the linear Ser—Ser sequence both in the presence and the absence of DTT, indicating the presence of the selenosulfide crosslink. The reduced binding of the Cys-Sec sequence compared to the Cys—Cys sequence in the absence of DTT is likely due to the point mutation which altered a proline in the reported sequence (Giebel, et al., supra) to a threonine. Taken together, these data demonstrate that a selenosulfide-constrained peptide is stable under conditions (10 mM DTT) where the corresponding disulfide-constrained sequence is reduced to the poorly-binding linear form. It can therefore be inferred that the selenosulfide crosslink would impart the same redox stability to a constrained peptide library as the sequences described here, allowing discovery of constrained peptide ligands even under reducing conditions.

What is claimed is:

1. A fusion protein, comprising: a selenocysteine-containing peptide fused to a surface protein displayed on an amplifiable genetic particle selected from a virus and a cell.

2. A fusion protein according to claim 1, wherein the covalent linkage between the selenocysteine-containing peptide and the surface protein is a peptide bond.

3. A fusion protein according to claim 1, wherein the selenocysteine-containing peptide is expressed by a DNA having a TGA codon and a selenocysteine insertion sequence.

4. A fusion protein according to claim 3, wherein the selenocysteine insertion sequence is located downstream of the TGA codon.

5. A fusion protein according to claim 1, wherein the selenocysteine is flanked on either or both sides by one or more randomized amino acids.

6. A fusion protein according to claim 1, wherein the selenocysteine in the peptide is positioned adjacent to one side of one or more randomized amino acids, the one or more randomized amino acids being flanked on a second side by a cysteine.

7. A fusion protein according to claim 1, wherein the selenocysteine in the peptide is capable of chemical derivatization of the selenol group.

8. A fusion protein according to claim 7, wherein the chemical derivatization results from a nucleophilic substitution reaction.

9. A fusion protein according to claim 7, wherein the chemical derivatization results from an oxidation reaction.

10. A fusion protein according to claim 7, wherein the chemical derivatization results from a metal coordination reaction.

11. A fusion protein according to claim 7, wherein a product of chemical derivatization of the selenocysteine in the peptide is a chemical functionality selected from the group consisting of enzyme substrates, enzyme cofactors, enzyme inhibitors, receptor ligands and cytotoxic agents.

12. A fusion protein according to claim 1, wherein the selenocysteine-containing peptide further comprises an enzyme substrate or is modified at the selenocysteine to form an enzyme substrate.

13. A fusion protein according to claim 12, wherein the enzyme substrate forms a reaction product in the presence of an enzyme and the enzyme substrate is located on the surface of the amplifiable genetic particle.

14. A fusion protein of claim 13, wherein the reaction product is capable of binding to an affinity substrate.

15. A fusion protein, according to claim 13, wherein the recombinant protein is selected from a library of variants of a single enzyme, wherein each variant contains one or more amino acid substitutions relative to the single enzyme.

16. A fusion protein according to claim 13, wherein the recombinant protein is selected from an expressed c-DNA library.

* * * * *

SEQUENCE LISTING

```
<160> NUMBER OF SEQ ID NOS: 42

<210> SEQ ID NO 1
<211> LENGTH: 38
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: N=A, G, C or U
<220> FEATURE:
<221> NAME/KEY: misc_feature
<222> LOCATION: (4)..(5)
<223> OTHER INFORMATION: N=A, G, C or U
<220> FEATURE:
<221> NAME/KEY: misc_feature
<222> LOCATION: (7)..(8)
<223> OTHER INFORMATION: N=A, G, C or U
<220> FEATURE:
<221> NAME/KEY: misc_feature
<222> LOCATION: (10)..(11)
<223> OTHER INFORMATION: N=A, G, C or U
<220> FEATURE:
<221> NAME/KEY: misc_feature
<222> LOCATION: (16)..(17)
<223> OTHER INFORMATION: N=A, G, C or U
<220> FEATURE:
<221> NAME/KEY: misc_feature
<222> LOCATION: (19)..(20)
<223> OTHER INFORMATION: N=A, G, C or U
<220> FEATURE:
<221> NAME/KEY: misc_feature
<222> LOCATION: (22)..(23)
<223> OTHER INFORMATION: N=A, G, C or U
<220> FEATURE:
<221> NAME/KEY: misc_feature
<222> LOCATION: (3)..(3)
<223> OTHER INFORMATION: K=G or U
<220> FEATURE:
<221> NAME/KEY: misc_feature
<222> LOCATION: (6)..(6)
<223> OTHER INFORMATION: K=G or U
<220> FEATURE:
<221> NAME/KEY: misc_feature
<222> LOCATION: (9)..(9)
<223> OTHER INFORMATION: K=G or U
<220> FEATURE:
<221> NAME/KEY: misc_feature
<222> LOCATION: (12)..(12)
<223> OTHER INFORMATION: K=G or U
<220> FEATURE:
<221> NAME/KEY: misc_feature
<222> LOCATION: (18)..(18)
<223> OTHER INFORMATION: K=G or U
<220> FEATURE:
```

```
<221> NAME/KEY: misc_feature
<222> LOCATION: (21)..(21)
<223> OTHER INFORMATION: K=G or U
<220> FEATURE:
<221> NAME/KEY: misc_feature
<222> LOCATION: (24)..(24)
<223> OTHER INFORMATION: K=G or U

<400> SEQUENCE: 1
nnknnknnkn nkugannknn knnkucggcc gaaacaug                           38

<210> SEQ ID NO 2
<211> LENGTH: 24
<212> TYPE: DNA
<213> ORGANISM: Artificial Sequence
<220> FEATURE:
<223> OTHER INFORMATION: synthetic

<400> SEQUENCE: 2
tcgtcttttc cttgaaagtc gcct                                          24

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
aagtgtacgc tttgatctat gctg                                          24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ttgcttttgc cttgaaatgt tctt                                          24

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atgactacgc agtgaccttc tctg                                          24

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
catattccgc cgtgaacgaa tcct                                          24

<210> SEQ ID NO 7
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 7
aaggctctgt gttgacagga ttcg                                              24

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
cttcttccgt gttgagctca gccg                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
catcatccga cttgagctaa gcag                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
atgcctccta cgtgaatggc tacg                                              24

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
aattggtttt cttgactgac tacg                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
ctgcatccga cgtgagctcg gcct                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13 gataggggc cttgagcgaa gatt                                               24

<210> SEQ ID NO 14
```

```
<210> SEQ ID NO 14
<211> LENGTH: 24
<212> TYPE: DNA
<213> ORGANISM: Artificial sequence
<220> FEATURE:
<223> OTHER INFORMATION: Synthetic

<400> SEQUENCE: 14
gcgtctttgc cttgaaggac gagt                                          24

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
ttgccgcgtc agtgatggtc tccg                                          24

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
ttgactggta cgtgatgtca gaat                                          24

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
gaggcgtcgc gttgatgttc gact                                          24

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
aagttggctc gttgatcggc gtcg                                          24

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
aatggggcgc agtgatcgag gcat                                          24

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
```
gcgagtccta cttgatttaa gccg                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
tgtgctcatc cgtgatctac tcgt                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
cagtcgacgc ggtgatggaa tgat                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
attgtggagt cgtgattgaa tccg                                              24

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
acgcagcgta tgtgattgcc gccc                                              24

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
gtgcagtata cgtgattgcc gaag                                              24

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
gctgggcagt cgtgatcgac tgat                                              24

<210> SEQ ID NO 27
<211> LENGTH: 24
<212> TYPE: DNA

<210> SEQ ID NO 28
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Sele;nocysteine

<400> SEQUENCE: 28

Ser Ala Arg Val Xaa His Gly Pro
1               5

<210> SEQ ID NO 29
<211> LENGTH: 98
<212> TYPE: DNA
<213> ORGANISM: Artificial Sequence
<220> FEATURE:
<223> OTHER INFORMATION: Synthetic

<400> SEQUENCE: 29
catgtttcgg ccgtaccgac cgattggtgc agacctgcaa ccgatgggcc gtgtcagaca     60
cgagcgctag agtgagaata gaaaggtacc cgggcatg                            98

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
catgcccggg tacctttcta ttctc                                          25

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ccctcatagt tagcgtaacg                                                20

<210> SEQ ID NO 32
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Selenocysteine

<400> SEQUENCE: 32

Ser Ala Arg Val Xaa His Gly Pro Ser Val
1               5                   10

<210> SEQ ID NO 33
<211> LENGTH: 85
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(36)
<223> OTHER INFORMATION: M = A or C
<220> FEATURE:
<221> NAME/KEY: misc_feature
<222> LOCATION: (39)..(39)
<223> OTHER INFORMATION: M = A or C
<220> FEATURE:
<221> NAME/KEY: misc_feature
<222> LOCATION: (42)..(42)
<223> OTHER INFORMATION: M = A or C
<220> FEATURE:
<221> NAME/KEY: misc_feature
<222> LOCATION: (48)..(48)
<223> OTHER INFORMATION: M = A or C
<220> FEATURE:
<221> NAME/KEY: misc_feature
<222> LOCATION: (51)..(51)
<223> OTHER INFORMATION: M = A or C
<220> FEATURE:
<221> NAME/KEY: misc_feature
<222> LOCATION: (54)..(54)
<223> OTHER INFORMATION: M = A or C
<220> FEATURE:
<221> NAME/KEY: misc_feature
<222> LOCATION: (57)..(57)
<223> OTHER INFORMATION: M = A or C
<220> FEATURE:
<221> NAME/KEY: misc_feature
<222> LOCATION: (37)..(38)
<223> OTHER INFORMATION: N = A, C, G or T
<220> FEATURE:
<221> NAME/KEY: misc_feature
<222> LOCATION: (40)..(41)
<223> OTHER INFORMATION: N = A, C, G or T
<220> FEATURE:
<221> NAME/KEY: misc_feature
<222> LOCATION: (43)..(44)
<223> OTHER INFORMATION: N = A, C, G or T
<220> FEATURE:
<221> NAME/KEY: misc_feature
<222> LOCATION: (49)..(50)
<223> OTHER INFORMATION: N = A, C, G or T
<220> FEATURE:
<221> NAME/KEY: misc_feature
<222> LOCATION: (52)..(53)
<223> OTHER INFORMATION: N = A, C, G or T
<220> FEATURE:
<221> NAME/KEY: misc_feature
<222> LOCATION: (55)..(56)
<223> OTHER INFORMATION: N = A, C, G or T
<220> FEATURE:
<221> NAME/KEY: misc_feature
<222> LOCATION: (58)..(59)
<223> OTHER INFORMATION: N = A, C, G or T

<400> SEQUENCE: 33
catgtttcgg ccgattggtg cagacctgca accgamnnmn nmnntcamnn mnnmnnmnna      60
gagtgagaat agaaaggtac ccggg                                          85

<210> SEQ ID NO 34
<211> LENGTH: 85
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (36)..(36)
<223> OTHER INFORMATION: M = A or C
<220> FEATURE:
<221> NAME/KEY: misc_feature
<222> LOCATION: (39)..(39)
<223> OTHER INFORMATION: M = A or C
<220> FEATURE:
<221> NAME/KEY: misc_feature
<222> LOCATION: (42)..(42)
<223> OTHER INFORMATION: M = A or C
<220> FEATURE:
<221> NAME/KEY: misc_feature
<222> LOCATION: (48)..(48)
<223> OTHER INFORMATION: M = A or C
<220> FEATURE:
<221> NAME/KEY: misc_feature
<222> LOCATION: (51)..(51)
<223> OTHER INFORMATION: M = A or C
<220> FEATURE:
<221> NAME/KEY: misc_feature
<222> LOCATION: (54)..(54)
<223> OTHER INFORMATION: M = A or C
<220> FEATURE:
<221> NAME/KEY: misc_feature
<222> LOCATION: (57)..(57)
<223> OTHER INFORMATION: M = A or C
<220> FEATURE:
<221> NAME/KEY: misc_feature
<222> LOCATION: (37)..(38)
<223> OTHER INFORMATION: N =  A, C, G or T
<220> FEATURE:
<221> NAME/KEY: misc_feature
<222> LOCATION: (40)..(41)
<223> OTHER INFORMATION: N =  A, C, G or T
<220> FEATURE:
<221> NAME/KEY: misc_feature
<222> LOCATION: (43)..(43)
<223> OTHER INFORMATION: N =  A, C, G or T
<220> FEATURE:
<221> NAME/KEY: misc_feature
<222> LOCATION: (49)..(50)
<223> OTHER INFORMATION: N =  A, C, G or T
<220> FEATURE:
<221> NAME/KEY: misc_feature
<222> LOCATION: (52)..(53)
<223> OTHER INFORMATION: N =  A, C, G or T
<220> FEATURE:
<221> NAME/KEY: misc_feature
<222> LOCATION: (55)..(56)
<223> OTHER INFORMATION: N =  A, C, G or T
<220> FEATURE:
<221> NAME/KEY: misc_feature
<222> LOCATION: (58)..(59)
<223> OTHER INFORMATION: N =  A, C, G or T

<400> SEQUENCE: 34
catgtttcgg ccgattggtg cagacctgca accgamnnmn nmnatcamnn mnnmnnmnna      60
gagtgagaat agaaaggtac ccggg                                           85

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Ser Ala Arg Val Leu Cys Asn His
1               5

<210> SEQ ID NO 36
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 36

His Pro Gln Gly Pro Pro
1               5

<210> SEQ ID NO 37
<211> LENGTH: 100
<212> TYPE: DNA
<213> ORGANISM: Artificial Sequence
<220> FEATURE:
<223> OTHER INFORMATION: Synthetic

<400> SEQUENCE: 37
catgtttcgg ccgattgatg aagcccagcc acgcttgggc cgtggctcgg tggaccttgc    60
ggatggcttt ccgcagagtg agaatagaaa ggtacccggg                         100

<210> SEQ ID NO 38
<211> LENGTH: 100
<212> TYPE: DNA
<213> ORGANISM: Artificial sequence
<220> FEATURE:
<223> OTHER INFORMATION: Synthetic

<400> SEQUENCE: 38
catgtttcgg ccgattgatg aagcccagcc acgcttgggc cgtggcacgg tggaccttgc    60
ggatggcatt ccgcagagtg agaatagaaa ggtacccggg                         100

<210> SEQ ID NO 39
<211> LENGTH: 100
<212> TYPE: DNA
<213> ORGANISM: Artificial Sequence
<220> FEATURE:
<223> OTHER INFORMATION: Synthetic

<400> SEQUENCE: 39
catgtttcgg ccgattggtg cagacctgca accgatgggc cgtgtcacgg tggaccttgc    60
ggatggcatt ccgcagagtg agaatagaaa ggtacccggg                         100

<210> SEQ ID NO 40
<211> LENGTH: 33
<212> TYPE: RNA
<213> ORGANISM: Artificial sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: N = G, A, U or C
<220> FEATURE:
<221> NAME/KEY: misc_feature
<222> LOCATION: (10)..(11)
<223> OTHER INFORMATION: N = G, A, U or C
<220> FEATURE:
<221> NAME/KEY: misc_feature
<222> LOCATION: (13)..(14)
<223> OTHER INFORMATION: N = G, A, U or C
<220> FEATURE:
<221> NAME/KEY: misc_feature
<222> LOCATION: (16)..(17)
<223> OTHER INFORMATION: N = G, A, U or C
<220> FEATURE:
<221> NAME/KEY: misc_feature
<222> LOCATION: (19)..(20)
<223> OTHER INFORMATION: N = G, A, U or C
<220> FEATURE:
```

```
<221> NAME/KEY: misc_feature
<222> LOCATION: (22)..(23)
<223> OTHER INFORMATION: N = G, A, U or C
<220> FEATURE:
<221> NAME/KEY: misc_feature
<222> LOCATION: (25)..(26)
<223> OTHER INFORMATION: N = G, A, U or C
<220> FEATURE:
<221> NAME/KEY: misc_feature
<222> LOCATION: (9)..(9)
<223> OTHER INFORMATION: K = U or G
<220> FEATURE:
<221> NAME/KEY: misc_feature
<222> LOCATION: (12)..(12)
<223> OTHER INFORMATION: K = U or G
<220> FEATURE:
<221> NAME/KEY: misc_feature
<222> LOCATION: (15)..(15)
<223> OTHER INFORMATION: K = U or G
<220> FEATURE:
<221> NAME/KEY: misc_feature
<222> LOCATION: (18)..(18)
<223> OTHER INFORMATION: K = U or G
<220> FEATURE:
<221> NAME/KEY: misc_feature
<222> LOCATION: (21)..(21)
<223> OTHER INFORMATION: K = U or G
<220> FEATURE:
<221> NAME/KEY: misc_feature
<222> LOCATION: (24)..(24)
<223> OTHER INFORMATION: K = U or G
<220> FEATURE:
<221> NAME/KEY: misc_feature
<222> LOCATION: (27)..(27)
<223> OTHER INFORMATION: K = U or G

<400> SEQUENCE: 40
gcgugcnnkn nknnknnknn knnknnkuga uaa                                        33

<210> SEQ ID NO 41
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(9)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = Selenocysteine

<400> SEQUENCE: 41

Ala Cys Xaa Xaa Xaa Xaa Xaa Xaa Xaa Xaa His Gly Pro Ser Val Ala
1               5                   10                  15

Gly Leu His Gln Ser Ala Glu
            20

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

His Pro Gln Gly Pro Thr
1               5
```